(12) United States Patent
Tian et al.

(10) Patent No.: US 11,453,724 B2
(45) Date of Patent: *Sep. 27, 2022

(54) RECOMBINANT BIFUNCTIONAL PROTEIN TARGETING CD47 AND HER2

(71) Applicant: ImmuneOnco Biopharmaceuticals (Shanghai) Co., Ltd., Shanghai (CN)

(72) Inventors: Wenzhi Tian, Shanghai (CN); Song Li, Shanghai (CN)

(73) Assignee: IMMUNEONCO BIOPHARMACEUTICALS (SHANGHAI) INC., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/535,075

(22) Filed: Aug. 8, 2019

(65) Prior Publication Data
US 2020/0048364 A1 Feb. 13, 2020

Related U.S. Application Data

(60) Provisional application No. 62/716,356, filed on Aug. 8, 2018.

(51) Int. Cl.
*C07K 16/32* (2006.01)
*C07K 14/705* (2006.01)
(Continued)

(52) U.S. Cl.
CPC .............. *C07K 16/32* (2013.01); *A61P 35/00* (2018.01); *C07K 14/70503* (2013.01); (Continued)

(58) Field of Classification Search
CPC .............. C07K 16/32; C07K 14/70503; C07K 2317/732; A61K 2039/505
See application file for complete search history.

(56) References Cited

U.S. PATENT DOCUMENTS 10,800,821 B2 * 10/2020 Tian ..................... A61P 19/02
10,973,878 B2 * 4/2021 Tian ..................... A61P 1/00
(Continued)

FOREIGN PATENT DOCUMENTS

CN 108864290 A1 11/2018
CN 109535258 A1 3/2019
(Continued)

OTHER PUBLICATIONS

Almagro & Fransson, Humanization of antibodies, Frontiers in Bioscience 2008; 13: 1619-33 (Year: 2008).*
(Continued)

*Primary Examiner* — Peter J Reddig
*Assistant Examiner* — Cheng Lu
(74) *Attorney, Agent, or Firm* — Duane Morris LLP; Thomas J. Kowalski; Deborah L. Lu

(57) ABSTRACT

The present disclosure provides a recombinant fusion protein containing an extracellular Ig-like domain of a signal-regulator protein (SIRP), linked via a linker, to a paratope of an Ig-like anti-HER2 antibody at the N-terminus of a heavy chain or a light chain constituting the paratope. The present disclosure also provides a polynucleotide encoding the recombinant fusion protein, an expression vector containing the polynucleotide, a method for producing the recombinant protein and a method for treating a disease caused by over-expression of CD47 and/or HER2.

10 Claims, 4 Drawing Sheets

Specification includes a Sequence Listing.

(51) Int. Cl.
*A61P 35/00* (2006.01)
*A61K 39/00* (2006.01)
*A61K 38/00* (2006.01)

(52) U.S. Cl.
CPC ........ *A61K 38/00* (2013.01); *A61K 2039/505* (2013.01); *C07K 2317/732* (2013.01); *C07K 2319/00* (2013.01)

(56) References Cited

U.S. PATENT DOCUMENTS

| | | | | |
|---|---|---|---|---|
| 2016/0177276 | A1* | 6/2016 | Lo | C07K 16/2827 424/134.1 |
| 2020/0095339 | A1* | 3/2020 | Tian | A61P 35/00 |
| 2020/0157223 | A1* | 5/2020 | Song | A61K 39/395 |
| 2021/0024598 | A1* | 1/2021 | Tian | C12N 5/10 |

FOREIGN PATENT DOCUMENTS

| | | |
|---|---|---|
| JP | 2003502062 A | 1/2003 |
| JP | 2017510249 A | 4/2017 |
| JP | 2017525698 A | 9/2017 |
| JP | 2017525755 A | 9/2017 |
| JP | 2018512850 A | 5/2018 |
| WO | 2016024021 A1 | 2/2016 |
| WO | 2016106158 A1 | 6/2016 |
| WO | 2019047885 A1 | 3/2019 |

OTHER PUBLICATIONS

Hatherley et al, The Structure of the Macrophage Signal Regulatory Protein (SIRP) Inhibitory Receptor Reveals a Binding Face Reminiscent of That Used by T Cell Receptors*, JBC, 282, 19, 14567-14575, Publication Date: May 11, 2007 (Year: 2007).*

ISA/CN, International Search Report and Written Opinion, dated Nov. 6, 2019, in co-pending international application PCT/CN2019/099530.

JPO, non-final office action of counterpart application JP2021-506322, prepared Jan. 25, 2022.

Hyunbo Shim, Bispecific Antibodies and Antibody-Drug Conjugates for Cancer Therapy: Technological Considerations, Biomolecules (2020) 10, 360, p. 1-31.

Shuhang Wang, et al., The State of the Art of Bispecific Antibodies for Treating Human Malignancies, EMBO Molecular Medicine (2021) 13: e14291. p. 1-13.

* cited by examiner

SEQUENCE LISTING

```
<160> NUMBER OF SEQ ID NOS: 22

<210> SEQ ID NO 1
<211> LENGTH: 375
<212> TYPE: DNA
<213> ORGANISM: Artificial Sequence
<220> FEATURE:
<223> OTHER INFORMATION: Nucleotides encoding first extracellular
      Ig-like domain of SIRPalpha

<400> SEQUENCE: 1
gaggaggagc tgcaggtgat tcagcctgac aagtccgtat cagttgcagc tggagagtcg       60
gccattctgc actgcactgt gacctccctg atccctgtgg ggcccatcca gtggttcaga      120
ggagctggac cagcccggga attaatctac aatcaaaaag aaggccactt ccccaggta       180 acaactgttt cagagtccac aaagagagaa acatggact tttccatcag catcagtgcc      240
atcaccccag cagatgccgg cacctactac tgtgtgaagt tccggaaagg gagccctgac      300
acggagttta agtctggagc aggcactgag ctgtctgtgc gtgccaaacc ctctgccccc     360
gtggtatcgg gccct                                                       375

<210> SEQ ID NO 2
<211> LENGTH: 125
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro
        115                 120                 125

<210> SEQ ID NO 3
```

```
<211> LENGTH: 45
<212> TYPE: DNA
<213> ORGANISM: Artificial Sequence
<220> FEATURE:
<223> OTHER INFORMATION: Nucleotides encoding linker

<400> SEQUENCE: 3
ggcggcggtg ggagcggcgg cggtgggagc ggcggcgggg gctcg              45

<210> SEQ ID NO 4
<211> LENGTH: 15
<212> TYPE: PRT
<213> ORGANISM: Artificial Sequence
<220> FEATURE:
<223> OTHER INFORMATION: Linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 1353
<212> TYPE: DNA
<213> ORGANISM: Artificial Sequence
<220> FEATURE:
<223> OTHER INFORMATION: Nucleotides encoding heavy chain of anti-HER2
      antibody

<400> SEQUENCE: 5
gaggtgcagc tggtcgagag cggcggggc ctcgtgcagc cgggcgggtc gctgcggctg     60
agctgcgccg cgagcgggtt caacatcaag gacacctaca tccactgggt gcgccaggcc    120
cccggcaagg gcctcgagtg ggtcgcccgg atctacccca cgaacgggta cacccgctac    180
gccgacagcg tgaagggccg gttcaccatc agcgcggaca cctcgaagaa cacggcctac    240
ctgcagatga acagcctgcg cgccgaggac accgccgtgt actactgcag ccggtggggc    300
ggcgacgggt tctacgccat ggactactgg ggcagggca ccctcgtcac cgtgagcagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tatgtggacg gcgtggaggt gcataatgcc aagacaaagc cgcgggagga gcagtacaac    900
gccacgtacc gtgtggtcag cgtcctcacc gtcctgcacc aagactggct gaatggcaag    960
gagtacaagt gcaaggtctc caacaaagcc ctcccagccc ccatcgccgc aaccatctcc   1020
aaagccaaag gcagccccg agaaccacag gtgtacaccc tgcccccatc ccgggaggag   1080
atgaccaaga accaagtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat tccaagctca ccgtggacaa gagcaggtgg   1260
cagcagggga acgtcttctc atgctccgtg atgcatgagg ctctgcacaa ccactacacg   1320
cagaagagcc tctccctgtc tccgggcaaa tga                               1353
```

<210> SEQ ID NO 6
<211> LENGTH: 450
<212> TYPE: PRT
<213> ORGANISM: Artificial Sequence
<220> FEATURE:
<223> OTHER INFORMATION: Heavy chain of anti-HER2 antibody

<400> SEQUENCE: 6

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ala Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Ala
                325                 330                 335

Ala Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 7
<211> LENGTH: 645
<212> TYPE: DNA
<213> ORGANISM: Artificial Sequence
<220> FEATURE:
<223> OTHER INFORMATION: Nucleotides encoding light chain of anti-HER2
      antibody

<400> SEQUENCE: 7
gacatccaga tgacccagag cccgtcgagc ctgagcgcca gcgtgggcga ccgggtcacg    60
atcacctgcc gcgcgagcca ggacgtgaac accgccgtgg cctggtacca gcagaagccc   120
gggaaggccc ccaagctcct gatctactcg gcgagcttcc tgtacagcgg cgtccccagc   180
cggttcagcg gtcgcgcag cggcaccgac ttcacgctca ccatcagcag cctgcagccg   240
gaggacttcg ccacctacta ctgccagcag cactacacca cgcccccac cttcgggcag   300 ggcaccaagg tggagatcaa gcgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                    645

<210> SEQ ID NO 8
<211> LENGTH: 214
<212> TYPE: PRT
<213> ORGANISM: Artificial Sequence
<220> FEATURE:
<223> OTHER INFORMATION: Light chain of anti-HER2 antibody

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 9
<211> LENGTH: 1773
<212> TYPE: DNA
<213> ORGANISM: Artificial Sequence
<220> FEATURE:
<223> OTHER INFORMATION: Nucleotides encoding SIRP alpha D1-Linker-anti-
      HER2 heavy chain

<400> SEQUENCE: 9

```
gaggaggagc tgcaggtgat tcagcctgac aagtccgtat cagttgcagc tggagagtcg      60
gccattctgc actgcactgt gaccctcctg atccctgtgg ggcccatcca gtggttcaga     120
ggagctggac cagcccggga attaatctac aatcaaaaag aaggccactt ccccccgggta    180
acaactgttt cagagtccac aaagagagaa acatggact  tttccatcag catcagtgcc    240
atcaccccag cagatgccgg cacctactac tgtgtgaagt tccggaaagg agccctgac     300
acggagttta gtctggagc  aggcactgag ctgtctgtgc gtgccaaacc ctctgccccc     360
gtggtatcgg gccctggcgg cggtgggagc ggcggcggtg ggagcggcgg cggggggctcg    420
gaggtgcagc tggtcgagag cggcggggc  ctcgtgcagc cgggcgggtc gctgcggctg    480
agctgcgccg cgagcgggtt caacatcaag gacacctaca tccactgggt gcgccaggcc     540
cccggcaagg gcctcgagtg ggtcgcccgg atctacccca cgaacgggta cacccgctac     600
gccgacagcg tgaagggccg gttcaccatc agcgcggaca cctcgaagaa cacggcctac     660
ctgcagatga acagcctgcg cgccgaggac accgccgtgt actactgcag ccggtggggc     720
ggcgacgggt tctacgccat ggactactgg gggcagggca cctcgtcac  cgtgagcagc    780
gctagcacca agggcccatc ggtcttcccc ctggcaccct cctccaagag cacctctggg     840
ggcacagcgg ccctgggctg cctggtcaag gactacttcc ccgaaccggt gacggtgtcg     900
tggaactcag gcgccctgac cagcggcgtg cacaccttcc cggctgtcct acagtcctca     960
ggactctact ccctcagcag cgtggtgacc gtgccctcca gcagcttggg cacccagacc    1020
tacatctgca acgtgaatca caagcccagc aacaccaagg tggacaagag agttgagccc    1080
aaatcttgtg acaaaactca cacatgccca ccgtgcccag cacctgaact cctgggggga    1140
ccgtcagtct tcctcttccc cccaaaaccc aaggacaccc tcatgatctc ccggacccct    1200
gaggtcacat gcgtggtggt ggacgtgagc cacgaagacc ctgaggtcaa gttcaactgg    1260
tatgtggacg gcgtggaggt gcataatgcc aagacaaagc cgcgggagga gcagtacaac    1320
```

```
gccacgtacc gtgtggtcag cgtcctcacc gtcctgcacc aagactggct gaatggcaag    1380
gagtacaagt gcaaggtctc caacaaagcc ctcccagccc ccatcgccgc aaccatctcc    1440
aaagccaaag gcagccccg agaaccacag gtgtacaccc tgcccccatc ccgggaggag     1500
atgaccaaga accaagtcag cctgacctgc ctggtcaaag gcttctatcc cagcgacatc   1560
gccgtggagt gggagagcaa tgggcagccg gagaacaact acaagaccac gcctcccgtg   1620
ctggactccg acggctcctt cttcctctat tccaagctca ccgtggacaa gagcaggtgg   1680
cagcagggga acgtcttctc atgctccgtg atgcatgagg ctctgcacaa ccactacacg   1740
cagaagagcc tctccctgtc tccgggcaaa tga                                 1773
```

<210> SEQ ID NO 10
<211> LENGTH: 590
<212> TYPE: PRT
<213> ORGANISM: Artificial Sequence
<220> FEATURE:
<223> OTHER INFORMATION: SIRP alpha D1-Linker-anti-HER2 heavy chain

<400> SEQUENCE: 10

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Gly Gly Gly
        115                 120                 125

Gly Ser Gly Gly Gly Ser Gly Gly Gly Ser Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Phe Asn Ile Lys Asp Thr Tyr Ile His Trp
                165                 170                 175

Val Arg Gln Ala Pro Gly Lys Gly Leu Glu Trp Val Ala Arg Ile Tyr
            180                 185                 190

Pro Thr Asn Gly Tyr Thr Arg Tyr Ala Asp Ser Val Lys Gly Arg Phe
        195                 200                 205

Thr Ile Ser Ala Asp Thr Ser Lys Asn Thr Ala Tyr Leu Gln Met Asn
    210                 215                 220

Ser Leu Arg Ala Glu Asp Thr Ala Val Tyr Tyr Cys Ser Arg Trp Gly
225                 230                 235                 240

Gly Asp Gly Phe Tyr Ala Met Asp Tyr Trp Gly Gln Gly Thr Leu Val
                245                 250                 255

Thr Val Ser Ser Ala Ser Thr Lys Gly Pro Ser Val Phe Pro Leu Ala
            260                 265                 270

Pro Ser Ser Lys Ser Thr Ser Gly Gly Thr Ala Ala Leu Gly Cys Leu
```

| | | | | | | | | | | | |
|---|---|---|---|---|---|---|---|---|---|---|---|
| | | 275 | | | | 280 | | | | 285 | |
| Val | Lys | Asp | Tyr | Phe | Pro | Glu | Pro | Val | Thr | Val | Ser | Trp | Asn | Ser | Gly |
| | | | | 290 | | | | | 295 | | | | | 300 | |

Val Lys Asp Tyr Phe Pro Glu Pro Val Thr Val Ser Trp Asn Ser Gly
275                 280                 285

Ala Leu Thr Ser Gly Val His Thr Phe Pro Ala Val Leu Gln Ser Ser
290                 295                 300
305                 310                 315                 320

Gly Leu Tyr Ser Leu Ser Ser Val Val Thr Val Pro Ser Ser Ser Leu
                325                 330                 335

Gly Thr Gln Thr Tyr Ile Cys Asn Val Asn His Lys Pro Ser Asn Thr
            340                 345                 350

Lys Val Asp Lys Arg Val Glu Pro Lys Ser Cys Asp Lys Thr His Thr
        355                 360                 365

Cys Pro Pro Cys Pro Ala Pro Glu Leu Leu Gly Gly Pro Ser Val Phe
370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                405                 410                 415

Lys Phe Asn Trp Tyr Val Asp Gly Val Glu Val His Asn Ala Lys Thr
            420                 425                 430

Lys Pro Arg Glu Glu Gln Tyr Asn Ala Thr Tyr Arg Val Val Ser Val
        435                 440                 445

Leu Thr Val Leu His Gln Asp Trp Leu Asn Gly Lys Glu Tyr Lys Cys
450                 455                 460

Lys Val Ser Asn Lys Ala Leu Pro Ala Pro Ile Ala Ala Thr Ile Ser
465                 470                 475                 480

Lys Ala Lys Gly Gln Pro Arg Glu Pro Gln Val Tyr Thr Leu Pro Pro
                485                 490                 495

Ser Arg Glu Glu Met Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 11
<211> LENGTH: 1065
<212> TYPE: DNA
<213> ORGANISM: Artificial Sequence
<220> FEATURE:
<223> OTHER INFORMATION: Nucleotides encoding SIRP alpha D1-Linker-anti-
      HER2 light chain

<400> SEQUENCE: 11
gaggaggagc tgcaggtgat tcagcctgac aagtccgtat cagttgcagc tggagagtcg     60
gccattctgc actgcactgt gacctccctg atccctgtgg ggcccatcca gtggttcaga    120
ggagctggac cagcccggga attaatctac aatcaaaaag aaggccactt ccccgggta    180 acaactgttt cagagtccac aaagagagaa aacatggact tttccatcag catcagtgcc    240
atcaccccag cagatgccgg cacctactac tgtgtgaagt tccggaaagg gagccctgac    300

```
acggagttta agtctggagc aggcactgag ctgtctgtgc gtgccaaacc ctctgccccc    360
gtggtatcgg gccctggcgg cggtgggagc ggcggcggtg ggagcggcgg cgggggctcg    420
gacatccaga tgacccagag cccgtcgagc ctgagcgcca gcgtgggcga ccgggtcacg    480
atcacctgcc gcgcgagcca ggacgtgaac accgccgtgg cctggtacca gcagaagccc    540
gggaaggccc ccaagctcct gatctactcg gcgagcttcc tgtacagcgg cgtcccagc    600 cggttcagcg gtcgcgcag cggcaccgac ttcacgctca ccatcagcag cctgcagccg    660
gaggacttcg ccacctacta ctgccagcag cactacacca cgcccccac cttcgggcag    720 ggcaccaagg tggagatcaa gcgaactgtg gctgcaccat ctgtcttcat cttcccgcca    780
tctgatgagc agttgaaatc tggaactgcc tctgttgtgt gcctgctgaa taacttctat    840
cccagagagg ccaaagtaca gtggaaggtg ataacgcccc tccaatcggg taactcccag    900
gagagtgtca cagagcagga cagcaaggac agcacctaca gcctcagcag caccctgacg    960
ctgagcaaag cagactacga gaaacacaaa gtctacgcct gcgaagtcac ccatcagggc   1020
ctgagctcgc ccgtcacaaa gagcttcaac aggggagagt gttag                   1065
```

<210> SEQ ID NO 12
<211> LENGTH: 354
<212> TYPE: PRT
<213> ORGANISM: Artificial Sequence
<220> FEATURE:
<223> OTHER INFORMATION: SIRP alpha D1-Linker-anti-HER2 light chain

<400> SEQUENCE: 12

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220
```

Thr Tyr Tyr Cys Gln Gln His Tyr Thr Thr Pro Thr Phe Gly Gln
225                 230                 235                 240

Gly Thr Lys Val Glu Ile Lys Arg Thr Val Ala Ala Pro Ser Val Phe
            245                 250                 255

Ile Phe Pro Pro Ser Asp Glu Gln Leu Lys Ser Gly Thr Ala Ser Val
        260                 265                 270

Val Cys Leu Leu Asn Asn Phe Tyr Pro Arg Glu Ala Lys Val Gln Trp
    275                 280                 285

Lys Val Asp Asn Ala Leu Gln Ser Gly Asn Ser Gln Glu Ser Val Thr
290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
            325                 330                 335

Thr His Gln Gly Leu Ser Ser Pro Val Thr Lys Ser Phe Asn Arg Gly
        340                 345                 350

Glu Cys

<210> SEQ ID NO 13
<211> LENGTH: 1101
<212> TYPE: DNA
<213> ORGANISM: Artificial Sequence
<220> FEATURE:
<223> OTHER INFORMATION: Nucleotides encoding SIRP alpha D1-Fc

<400> SEQUENCE: 13

```
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt ccccgggta     180
acaactgttt cagagtccac aaagagagaa acatggact tttccatcag catcagtgcc     240
atcaccccag cagatgccgg cacctactac tgtgtgaagt tccggaaagg gagccctgac     300
acggagttta gtctggagc aggcactgag ctgtctgtgc gtgccaaacc ctctgccccc     360
gtggtatcgg gccctgcggc gagggccaca cctcagcacg aattcgagcc caaatcttgt     420
gacaaaactc acacatgccc accgtgccca gcacctgaac tcctgggggg accgtcagtc     480
ttcctcttcc cccaaaaacc caaggacacc ctcatgatct cccggaccccc tgaggtcaca     540
tgcgtggtgg tggacgtgag ccacgaagac cctgaggtca agttcaactg gtacgtggac     600
ggcgtggagg tgcataatgc caagacaaag ccgcgggagg agcagtacaa cagcacgtac     660
cgtgtggtca gcgtcctcac cgtcctgcac caggactggc tgaatggcaa ggagtacaag     720
tgcaaggtct ccaacaaagc cctcccagcc ccatcgaga aaaccatctc caaagccaaa     780
gggcagcccc gagaaccaca ggtgtacacc ctgcccccat cccgggatga gctgaccaag     840
aaccaggtca gcctgacctg cctggtcaaa ggcttctatc ccagcgacat cgccgtggag     900
tgggagagca atgggcagcc ggagaacaac tacaagacca cgcctcccgt gctggactcc     960
gacggctcct tcttcctcta cagcaagctc accgtggaca gagcaggtg gcagcagggg    1020
aacgtcttct catgctccgt gatgcatgag gctctgcaca accactacac gcagaagagc    1080
ctctccctgt ctccgggttg a                                              1101
```

<210> SEQ ID NO 14
<211> LENGTH: 366
<212> TYPE: PRT
<213> ORGANISM: Artificial Sequence
<220> FEATURE:
<223> OTHER INFORMATION: SIRP alpha D1-Fc

<400> SEQUENCE: 14

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Glu Phe Glu Pro Lys Ser Cys Asp Lys Thr His
130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly
        355                 360                 365
```

<210> SEQ ID NO 15
<211> LENGTH: 1749
<212> TYPE: DNA
<213> ORGANISM: Artificial Sequence
<220> FEATURE:
<223> OTHER INFORMATION: Nulcoetides encoding SIRP alpha D1-Linker-anti-
EGFR light chain

<400> SEQUENCE: 15

```
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt ccccgggta      180
acaactgttt cagagtccac aaagagagaa acatggact tttccatcag catcagtgcc     240
atcaccccag cagatgccgg cacctactac tgtgtgaagt ccggaaagg gagccctgac     300
acggagttta agtctggagc aggcactgag ctgtctgtgc gtgccaaacc ctctggcggc    360
ggtgggagcg gcggcggtgg gagcggcggc ggggctcgc aggtgcagct gaagcagtca     420
ggacctggcc tagtgcagcc ctcacagagc ctgtccatca cctgcacagt tctggttc      480
tcattaacta ctatggtgt acactgggtt cgccagtctc caggaaaggg tctggagtgg     540
ctgggagtga tatggagtgg tggaaacaca gactataata cccttcac atccagactg      600
agcatcaaca aggacaattc caagagccaa gttttctta aaatgaacag tctgcaatct     660
caggacacag ccatatatta ctgtgccaga gccctcacct actatgatta cgagtttgct     720
tactggggcc aagggactct ggtcactgtc tctgcagcta gcaccaaggg cccatcggtc    780
ttcccctgg caccctcctc aagagcacc tctggggca gcggccct gggctgcctg          840
gtcaaggact acttccccga accggtgacg gtgtcgtgga actcaggcgc cctgaccagc    900
ggcgtgcaca ccttcccggc tgtcctacag tcctcaggac tctactccct cagcagcgtg    960
gtgaccgtgc cctccagcag cttgggcacc cagacctaca tctgcaacgt gaatcacaag   1020
cccagcaaca ccaaggtgga caagagagtt gagcccaaat cttgtgacaa aactcacaca   1080
tgcccaccgt gcccagcacc tgaactcctg ggggaccgt cagtcttcct cttcccccca    1140
aaacccaagg acaccctcat gatctcccgg acccctgagg tcacatgcgt ggtggtggac   1200
gtgagccacg aagaccctga ggtcaagttc aactggtatg tggacggcgt ggaggtgcat   1260
aatgccaaga caaagccgcg ggaggagcag tacaacgcca cgtaccgtgt ggtcagcgtc   1320
ctcaccgtcc tgcaccaaga ctggctgaat ggcaaggagt acaagtgcaa ggtctccaac   1380
aaagccctcc cagcccccat cgccgcaacc atctccaaag ccaaagggca gccccgagaa   1440
ccacaggtgt acaccctgcc cccatcccgg gaggagatga ccaagaacca gtcagcctg    1500
acctgcctgg tcaaaggctt ctatcccagc gacatcgccg tggagtggga gagcaatggg   1560
cagccggaga caactacaa gaccacgcct cccgtgctgg actccgacgg ctccttcttc    1620
ctctattcca agctcaccgt ggacaagagc aggtggcagc aggggaacgt cttctcatgc   1680
tccgtgatgc atgaggctct gcacaaccac tacacgcaga agagcctctc cctgtctccg   1740
ggcaaatga                                                           1749
```

<210> SEQ ID NO 16
<211> LENGTH: 582
<212> TYPE: PRT
<213> ORGANISM: Artificial Sequence
<220> FEATURE:
<223> OTHER INFORMATION: SIRP alpha D1-Linker-anti-EGFR light chain

<400> SEQUENCE: 16

Glu Glu Glu Leu Gln Val Ile Gln Pro Asp Lys Ser Val Ser Val Ala
1               5                   10                  15

```
Ala Gly Glu Ser Ala Ile Leu His Cys Thr Val Thr Ser Leu Ile Pro
             20                  25                  30

Val Gly Pro Ile Gln Trp Phe Arg Gly Ala Gly Pro Ala Arg Glu Leu
         35                  40                  45

Ile Tyr Asn Gln Lys Glu Gly His Phe Pro Arg Val Thr Thr Val Ser
     50                  55                  60

Glu Ser Thr Lys Arg Glu Asn Met Asp Phe Ser Ile Ser Ile Ser Ala
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser Gly Gly Gly Ser Gly Gly Gly Gly Ser
        115                 120                 125

Gly Gly Gly Gly Ser Gln Val Gln Leu Lys Gln Ser Gly Pro Gly Leu
        130                 135                 140

Val Gln Pro Ser Gln Ser Leu Ser Ile Thr Cys Thr Val Ser Gly Phe
145                 150                 155                 160

Ser Leu Thr Asn Tyr Gly Val His Trp Val Arg Gln Ser Pro Gly Lys
                165                 170                 175

Gly Leu Glu Trp Leu Gly Val Ile Trp Ser Gly Gly Asn Thr Asp Tyr
            180                 185                 190

Asn Thr Pro Phe Thr Ser Arg Leu Ser Ile Asn Lys Asp Asn Ser Lys
            195                 200                 205

Ser Gln Val Phe Phe Lys Met Asn Ser Leu Gln Ser Gln Asp Thr Ala
    210                 215                 220

Ile Tyr Tyr Cys Ala Arg Ala Leu Thr Tyr Tyr Asp Tyr Glu Phe Ala
225                 230                 235                 240

Tyr Trp Gly Gln Gly Thr Leu Val Thr Val Ser Ala Ala Ser Thr Lys
                245                 250                 255

Gly Pro Ser Val Phe Pro Leu Ala Pro Ser Ser Lys Ser Thr Ser Gly
            260                 265                 270

Gly Thr Ala Ala Leu Gly Cys Leu Val Lys Asp Tyr Phe Pro Glu Pro
            275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Ser Leu Gly Thr Gln Thr Tyr Ile Cys Asn
                325                 330                 335

Val Asn His Lys Pro Ser Asn Thr Lys Val Asp Lys Arg Val Glu Pro
            340                 345                 350

Lys Ser Cys Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
        370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ala Thr Tyr Arg Val Val Ser Val Leu Thr Val Leu His Gln Asp Trp
```

```
                435                 440                 445
Leu Asn Gly Lys Glu Tyr Lys Cys Lys Val Ser Asn Lys Ala Leu Pro
450                 455                 460
Ala Pro Ile Ala Ala Thr Ile Ser Lys Ala Lys Gly Gln Pro Arg Glu
465                 470                 475                 480
Pro Gln Val Tyr Thr Leu Pro Pro Ser Arg Glu Glu Met Thr Lys Asn
                485                 490                 495
Gln Val Ser Leu Thr Cys Leu Val Lys Gly Phe Tyr Pro Ser Asp Ile
            500                 505                 510
Ala Val Glu Trp Glu Ser Asn Gly Gln Pro Glu Asn Asn Tyr Lys Thr
            515                 520                 525
Thr Pro Pro Val Leu Asp Ser Asp Gly Ser Phe Phe Leu Tyr Ser Lys
            530                 535                 540
Leu Thr Val Asp Lys Ser Arg Trp Gln Gln Gly Asn Val Phe Ser Cys
545                 550                 555                 560
Ser Val Met His Glu Ala Leu His Asn His Tyr Thr Gln Lys Ser Leu
                565                 570                 575
Ser Leu Ser Pro Gly Lys
            580

<210> SEQ ID NO 17
<211> LENGTH: 645
<212> TYPE: DNA
<213> ORGANISM: Artificial Sequence
<220> FEATURE:
<223> OTHER INFORMATION: Nucleotides encoding Light chain of anti-EGFR
      antibody

<400> SEQUENCE: 17
gacatcttgc tgactcagtc tccagtcatc ctgtctgtga gtccaggaga aagagtcagt     60
ttctcctgca gggccagtca gagtattggc acaaacatac actggtatca gcaaagaaca    120
aatggttctc caaggcttct cataaagtat gcttctgagt ctatctctgg gatcccttcc    180
aggtttagtg gcagtggatc agggacagat tttactctta gcatcaacag tgtggagtct    240
gaagatattg cagattatta ctgtcaacaa aataataact ggccaaccac gttcggtgct    300
gggaccaagc tggagctgaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 18
<211> LENGTH: 214
<212> TYPE: PRT
<213> ORGANISM: Artificial Sequence
<220> FEATURE:
<223> OTHER INFORMATION: Light chain of anti-EGFR antibody

<400> SEQUENCE: 18

Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
```

-continued

```
                    35                  40                  45
Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 19
<211> LENGTH: 57
<212> TYPE: DNA
<213> ORGANISM: Artificial Sequence
<220> FEATURE:
<223> OTHER INFORMATION: Nucleotides encoding signal peptide

<400> SEQUENCE: 19
atgggatggt catgtatcat ccttttttctg gtagcaactg caactggagt acattca      57

<210> SEQ ID NO 20
<211> LENGTH: 9
<212> TYPE: DNA
<213> ORGANISM: Artificial Sequence
<220> FEATURE:
<223> OTHER INFORMATION: Kozak

<400> SEQUENCE: 20 gccgccacc      9

<210> SEQ ID NO 21
<211> LENGTH: 8
<212> TYPE: PRT
<213> ORGANISM: Artificial Sequence
<220> FEATURE:
<223> OTHER INFORMATION: Linker

<400> SEQUENCE: 21

Gly Gly Gly Gly Gly Gly Gly Gly
1               5

<210> SEQ ID NO 22
<211> LENGTH: 15
<212> TYPE: PRT
<213> ORGANISM: Artificial Sequence
<220> FEATURE:
<223> OTHER INFORMATION: Linker

```
<400> SEQUENCE: 22

Gly Gly Gly Gly Ser Gly Gly Gly Gly Ser Gly Gly Gly Gly Ser
1               5                   10                  15
```

US 11,453,724 B2

RECOMBINANT BIFUNCTIONAL PROTEIN TARGETING CD47 AND HER2

FIELD OF THE INVENTION

The present disclosure relates to a recombinant fusion protein targeting CD47 and HER2, and the preparation and use thereof, especially its use in tumor therapies.

SEQUENCE LISTING

The instant application contains a Sequence Listing which has been submitted electronically in ASCII format and is hereby incorporated by reference in its entirety. Said ASCII copy, is named, 5552500019SL.txt and is 39.0 kbytes in size.

BACKGROUND OF THE INVENTION

Antibody therapies are approved in various jurisdictions to treat a wide range of cancers, and have significantly improved patient outcomes (Komeev K V et al., (2017) TLR-signaling and proinflammatory cytokines as drivers of tumorigenesis. *Cytokine* 89: 127-135). Once bound to a cancer antigen, antibodies may induce antibody-dependent cell-mediated cytotoxicity, activate the complement system, or prevent a receptor from interacting with its ligand, all of which may lead to cell death. U.S. FDA-approved antibody drugs include Alemtuzumab, Nivolumab, Rituximab and Durvalumab.

Tumor Evasion of Immune Surveillance

Cancer cells have developed several mechanisms to evade a host's immune surveillance. For example, many tumor or cancer cells express on their surfaces a high level of CD47, which, by binding to the SIRPα (Signal regulatory protein alpha; also known as SHPS1 and BIT) on the cell surface of macrophages, inhibit phagocytosis of the cancer cells by macrophages.

Cancer cells over-expressing CD47 are found in patients with acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer. Injection of CD-47 specific antibody that blocks CD47-SIRPα interaction can significantly inhibit tumor growth in tumor-bearing mice, and tumor or cancer cells were eliminated completely when the same antibody was injected into mice carrying human leukemia cells (Theocharides A P A et al., (2012) *J. C. Y. J. Exp. Med.* 209:1883-1899).

HER2 Associated Tumor and Treatment

HER2, also known as ErbB2, is a member of the human epidermal growth factor receptor family, and encoded by the erythroblastic oncogene B (ERBB2). Overexpression of this oncogene occurs in approximately 15-30% of breast cancers, and is strongly associated with increased disease recurrence and a poor prognosis (Mitri Z et al., (2012) *Chemotherapy Research and Practice*. Volume 2012, Article ID 743193, 7 pages; Burstein H J, (2005) *The New England Journal of Medicine*. 353 (16): 1652-4; Tan M, et al., (2007) *Advances in Experimental Medicine and Biology*. 608: 119-29). Such overexpression is also found in ovarian cancer, stomach cancer, adenocarcinoma of the lung and aggressive forms of uterine cancer.

Monoclonal antibodies have been or are being developed to target HER2. One such antibody, Trastuzumab (Herceptin®), was approved for medical use in the United States in 1998 and has been successfully used in clinical treatment of HER2 positive breast cancers.

Therapeutic Bi-Specific or Multi-Specific Fusion Proteins/Antibodies

Antibodies have significantly advanced our ability to treat cancers, yet clinical studies have shown many patients do not adequately respond to monospecific therapy. For example, in breast cancer treatment, a substantial percentage of HER2-positive patients do not respond to Trastuzumab treatment due to a number of mechanisms, including the 158F polymorphisms of the FcgRIIIA gene. Additionally, acquired antibody resistance frequently occurs following several cycles of treatment.

Therefore, bispecific or multi-specific antibodies are developed against two or more separate and unique antigens, or different epitopes of the same antigen. For example, some bispecific antibodies are engineered to simultaneously bind a cytotoxic cell and a tumor cell. Such antibodies are capable of blocking multiple tumor cell growth and survival pathways, and/or activating tumor cell killing pathways, and thus have a potential to better inhibit cancer growth.

However, bispecific or multi-specific antibodies present significant design challenges as a number of issues have to be considered, including compatibility of the molecules, the resulting antibody's affinity, stability and pharmaceutical properties. It is well recognized that simply linking antibodies or proteins together does not necessarily result in synergetic/advantageous effects. A recombinant antibody disclosed in the present disclosure, comprising SIRPαD1, linked by a linker, to Erbitux (Cetuximab), has been proved to have inferior anti-tumor activity compared to Erbitux or SIRPαD1-Fc alone in the HT-29 or NCl-H1975 tumor model (see Example 8).

Through diligent efforts, the present inventors, however, have successfully designed a recombinant bispecific protein that accurately targets both CD47 and HER2 and shows better anti-tumor activity than ordinary single antigen targeting antibodies.

SUMMARY OF THE INVENTION

The present disclosure discloses a recombinant fusion protein, comprising an extracellular Ig-like domain of a signal-regulator protein (SIRP), linked via a linker, to a paratope of an Ig-like anti-HER2 antibody at the N-terminus of a heavy chain or a light chain constituting the paratope, wherein the recombinant fusion protein bind to CD47, HER2 and FcR simultaneously. Binding to CD47s on cancer cells blocks the interaction of CD47s with SIRPs on macrophages and thus releases the check on macrophages by SIRP-mediated inhibitory signals; while binding to HER2s on cancer cells inhibits the uncontrolled tumor cell growth; and at the same time, binding to FcRs on NK cells or macrophages stimulates targeted cancer cell killings by NK cells or macrophages.

In an embodiment, either paratope of the Ig-like anti-HER2 antibody is linked to an extracellular Ig-like domain of signal-regulator protein (SIRP) at the N-terminus of the heavy chain or the light chain constituting the paratope. In an embodiment, each paratope of the Ig-like anti-HER2 antibody is linked to an extracellular Ig-like domain of signal-regulator protein (SIRP) at the N-terminus of the heavy chain or the light chain constituting that paratope. In one embodiment, each paratope of the Ig-like anti-HER2 antibody is linked to an extracellular Ig-like domain of signal-regulator protein (SIRP) at the N-terminus of the heavy chain constituting that paratope. In one embodiment, each paratope of the Ig-like anti-HER2 antibody is linked to an extracellular Ig-like domain of signal-regulator protein (SIRP) at the N-terminus of the light chain constituting that paratope. In one embodiment, one paratope of the Ig-like anti-HER2 antibody is linked to an extracellular Ig-like domain of signal-regulator protein (SIRP) at the N-terminus of the heavy chain constituting that paratope, and the other paratope is linked to an extracellular Ig-like domain of signal-regulator protein (SIRP) at the N-terminus of the light chain constituting that paratope. In some embodiment, one paratope of the anti-HER2 antibodies may be linked to two copies of the extracellular Ig-like domain of signal-regulator protein (SIRP) at the N-terminus of the heavy chain and light chain constituting that paratope.

In one embodiment, the signal-regulatory protein in the recombinant fusion protein may be SIRPα, and the extracellular Ig-like domain of the signal-regulatory protein may be the first extracellular Ig-like domain of SIRPα (SIRPαD1). The extracellular Ig-like domain of the signal-regulatory protein, such as SIRPαD1, can bind to CD47 on the cell surfaces of cancer/tumor cells and thus block the interaction of CD47 with SIRPs on the cell surfaces of macrophages.

In one embodiment, the SIRPαD1 has the nucleic acid sequence and amino acid sequence set forth in SEQ ID NOs: 1 and 2, respectively. In some embodiments, the SIRPαD1 may comprise an amino acid sequence having at least 80%, 85%, 90%, 95%, 98% or 99% identity to SEQ ID NO: 2, wherein the SIRPαD1 can bind to CD47 on the cell surfaces of cancer/tumor cells and block the interaction of CD47 with SIRPs on the cell surfaces of macrophages.

The linker in the recombinant fusion protein may be a peptide of about 5 to 30 amino acid residues. In an embodiment, the linker is a peptide of 10 to 30 amino acid residues. In another embodiment, the linker is a peptide of 15 to 30 amino acid residues. In some embodiments, the linker is -(Gly-Gly-Gly-Gly-Ser)$_3$- (SEQ ID NO: 4), which may be encoded by SEQ ID NO: 3.

The anti-HER2 antibody may be an isolated monoclonal antibody, such as Trastuzumab, Margetuximab, and antibodies having at least 80%, 85%, 90%, 95%, 98% or 99% amino acid identity to Trastuzumab or Margetuximab while remaining the binding affinity.

The anti-HER2 antibody may be an isolated monoclonal antibody, comprising two heavy chains each having an amino acid sequence of SEQ ID NO: 6, and two light chains each having an amino acid sequence of SEQ ID NO: 8, which may be encoded by nucleic acid sequences of SEQ ID NOs: 5 and 7, respectively. The antigen-binding (Fab) or paratope portion of the anti-HER2 antibody can bind to HER2 on the cell surfaces of cancer/tumor cells and thus prevent uncontrolled tumor/cancer cell growth from occurring, while the Fc portion of the anti-HER2 antibody can bind to FcRs on the cell surfaces of NK cells or macrophages to stimulate cancer cell killings by the NK cells or macrophages. In some embodiments, the heavy chain may comprise an amino acid sequence having at least 80%, 85%, 90%, 95%, 98% or 99% identity to SEQ ID NO: 6, wherein the anti-HER2 antibody is able to bind to HER2 and prevent uncontrolled growth of cancer/tumor cells, and is also able to bind to FcRs on the cell surfaces of NK cells or macrophages and thus activate the NK cells or macrophages for killing the cancer cells. In some embodiments, the light chain may comprise an amino acid sequence having at least 80%, 85%, 90%, 95%, 98% or 99% identity to SEQ ID NO: 8, wherein the anti-HER2 antibody is able to bind to HER2 and prevent occurring of uncontrolled growth of cancer/tumor cells.

The SIRPαD1-Linker-anti-HER2 heavy chain fusion protein may comprise an amino acid sequence of SEQ ID NO: 10, which may be encoded by nucleotide of SEQ ID NO: 9. In some embodiments, the SIRPαD1-Linker-anti-HER2 heavy chain comprises an amino acid sequence having at least 80%, 85%, 90%, 95%, 98% or 99% identity to SEQ ID NO: 10, wherein the SIRPαD1-Linker-anti-HER2 heavy chain together with the light chain of an anti-HER2 antibody can bind to CD47, HER2 and FcR, i) blocking the interaction of CD47 on cancer cells with SIRPs on macrophages; ii) inhibiting uncontrolled cancer/tumor cell growth; and iii) stimulating cancer cell killings by NK cells or macrophages.

In one embodiment, the SIRPαD1-Linker-anti-HER2 light chain fusion protein comprises an amino acid sequence of SEQ ID NO: 12, which may be encoded by nucleotide of SEQ ID NO: 11. In some embodiments, the SIRPαD1-Linker-anti-HER2 light chain comprises an amino acid sequence having at least 80%, 85%, 90%, 95%, 98% or 99% identity to SEQ ID NO: 10, wherein the SIRPαD1-Linker-anti-HER2 light chain together with the heavy chain of an anti-HER2 antibody can bind to CD47, HER2 and FcR, i) blocking the interaction of CD47 on cancer cells with SIRPs on macrophages; ii) inhibiting uncontrolled cancer/tumor cell growth; and iii) stimulating cancer cell killings by NK cells or macrophages.

A nucleic acid molecule encoding the recombinant fusion protein of the present disclosure is also provided, as well as an expression vector comprising the nucleic acid and a host cell comprising the expression vector.

A method for preparing the recombinant fusion protein using the host cell comprising the expression vector is also provided, and comprises steps of (i) expressing the recombinant fusion protein in the host cell and (ii) isolating the recombinant fusion protein from the host cell.

In another respect, the present disclosure provides a pharmaceutical composition, comprising the recombinant fusion protein of the present disclosure, and at least one pharmaceutically acceptable carrier. The pharmaceutical composition may further comprise at least one adjuvant.

In another aspect, the present disclosure provides a method for treating a disease caused by over-expression of CD47 and/or HER2, comprising administering to a patient or a subject in need thereof a therapeutically effective amount of the pharmaceutical composition of the present disclosure.

In one embodiment, the present disclosure provides the use of the recombinant fusion protein in the manufacture of a pharmaceutical composition for the treatment of a disease caused by over-expression of CD47 and/or HER2.

In one embodiment, the method of the present disclosure is for treating a disease selected from the group consisting of acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, and renal cell carcinoma. In one embodiment, the present disclosure provides a method for treating Crohn's disease, allergic asthma or rheumatoid arthritis.

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
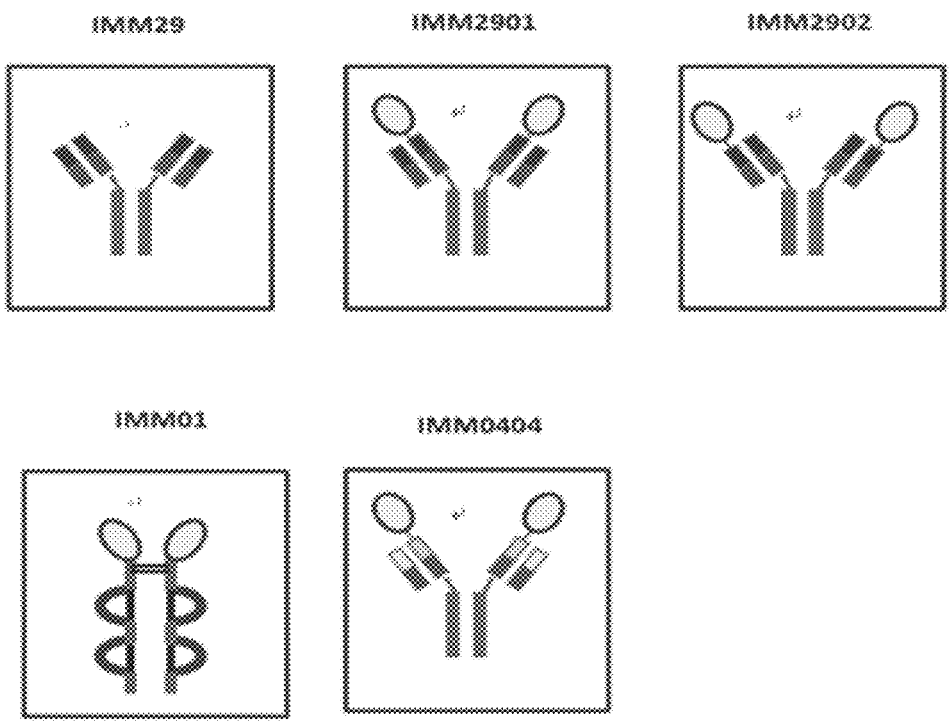
FIG. 1 is a schematic diagram of the structures of the recombinant fusion proteins of the present disclosure.

There are principally three different approaches to targeting two or more pharmacologies of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems may reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single entity. The design and validation of such multifunctional entities are more complex and require substantial investigation into the optimal ratio of target activities. Multifunctional molecules may also be amenable to fixed dose combination with other drugs thereby combining three or even four pharmacologies in a single pill to produce further increments in efficacy.

A recombinant bispecific or multi-specific protein against two or more targets is a multifunctional drug, which does not necessarily show superior anti-tumor activity compared to ordinary single antigen targeting antibodies. For example, as shown in the Example 8 below, a recombinant antibody comprising SIRPαD1, linked by a linker, to Erbitux (Cetuximab), an anti-EGFR antibody, had lower anti-tumor activity than Erbitux or SIRPαD1-Fc in the HT-29 or NCl-H1975 tumor model. Smart designs are needed for a recombinant protein to provide synergistic effects.

Through diligent experimentation, the present inventors have invented a novel recombinant fusion protein, which can attack tumors, via three mechanisms of actions, one to release the check on macrophages by SIRP-mediated inhibitory signals, one to control HER2 signaling mediated tumor/cancer cell proliferation, the third to stimulate cancer cell killings by NK cells and/or macrophages.

The recombinant fusion protein of the present disclosure comprises comprising an extracellular Ig-like domain of a signal-regulator protein (SIRP), linked via a linker, to a paratope of an Ig-like anti-HER2 antibody at the N-terminus of a heavy chain or a light chain constituting the paratope, wherein the recombinant fusion protein bind to CD47, HER2 and FcR simultaneously, i) binding to CD47s on cancer cells to block the interaction of CD47s with SIRPs on macrophages and thus releasing the check on macrophages by SIRP-mediated inhibitory signals; ii) binding to HER2 on cancer cells and thus inhibiting uncontrolled tumor/cancer cell growth; and iii) binding to FcRs on NK cells or macrophages to stimulate cancer cell killings by NK cells or macrophages. In an embodiment, either paratope of the Ig-like anti-HER2 antibody is linked to an extracellular Ig-like domain of signal-regulator protein (SIRP) at the N-terminus of the heavy chain or the light chain constituting the paratope. In an embodiment, each paratope of the Ig-like anti-HER2 antibody is linked to an extracellular Ig-like domain of signal-regulator protein (SIRP) at the N-terminus of the heavy chain or the light chain constituting that paratope. In one embodiment, each paratope of the Ig-like anti-HER2 antibody is linked to an extracellular Ig-like domain of signal-regulator protein (SIRP) at the N-terminus of the heavy chain constituting that paratope. In one embodiment, each paratope of the Ig-like anti-HER2 antibody is linked to an extracellular Ig-like domain of signal-regulator protein (SIRP) at the N-terminus of the light chain constituting that paratope. In one embodiment, one paratope of the Ig-like anti-HER2 antibody is linked to an extracellular Ig-like domain of signal-regulator protein (SIRP) at the N-terminus of the heavy chain constituting that paratope, and the other paratope is linked to an extracellular Ig-like domain of signal-regulator protein (SIRP) at the N-terminus of the light chain constituting that paratope. In some embodiment, one paratope of the anti-HER2 antibodies may be linked to two copies of the extracellular Ig-like domain of signal-regulator protein (SIRP) at the N-terminus of the heavy chain and light chain constituting that paratope.

The three main components contained in the fusion protein of the present disclosure are an extracellular Ig-like domain of a signal-regulator protein (SIRP), a linker, and an anti-HER2 antibody. A person of ordinary skills in the art will recognize that there are many design choices for selecting the above three components. Preferably, human-derived sequence is used in human cancer therapies, as the strong immunogenicity of the proteins or peptides from non-human animals may lead to allergy and other adverse effects. However, other animal proteins or peptides, humanized if appropriate, may also be used in the present disclosure based on different application purposes.

Any extracellular Ig-like domain of any SIPR (SIRPα, SIRPβ, and SIRPγ) capable of binding with CD47 may be selected for construction of the fusion protein. In one embodiment, the signal-regulatory protein in the recombinant fusion protein is SIRPα, and the extracellular Ig-like domain of the signal-regulatory protein is the first extracellular Ig-like domain of SIRPα (SIRPαD1).

In one embodiment, the recombinant fusion protein comprises SIRPαD1 having the nucleic acid sequence and amino acid sequence set forth in SEQ ID Nos: 1 and 2, respectively. In another embodiment, the SIRPαD1 may comprise an amino acid sequence having at least 80%, 85%, 90%, 95%, 98% or 99% identity to SEQ ID NO: 2, wherein the SIRPαD1 can bind to CD47 on the cell surface of cancer/tumor cells and block the interaction of CD47 with SIRPs on the cell surfaces of macrophages.

Linkers serve primarily as a spacer between the extracellular Ig-like domain of SIRP and the N-terminus of the heavy or light chain of an anti-HER2 antibody. The linker may be made up of amino acids linked together by peptide bonds, preferably from 5 to 30 amino acids linked by peptide bonds, wherein the amino acids are selected from the 20 naturally occurring amino acids. When two copies of the SIRP extracellular Ig-like domain are linked to one paratope of the anti-HER2 antibody at the N-terminus of the heavy chain and the light chain constituting that paratope, a relatively long linker, maybe of 10 or more, or even 15 or more amino acid resides in length, may be needed to avoid possible stereo hindrance. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, (Gly)$_8$ (SEQ ID NO: 21), poly(Gly-Ala), and polyalanines. One exemplary suitable linker as shown in the Examples below is poly(Gly-Ser), such as -(Gly-Gly-Gly-Gly-Ser)$_3$- (SEQ ID NO: 22).

Linkers may also be non-peptide linkers. For example, alkyl linkers such as —NH—, —(CH$_2$)s-C(O)—, wherein s=2-20 can be used. These alkyl linkers may further be substituted by any non-sterically hindering group such as lower alkyl (e.g., C$_{1-4}$) lower acyl, halogen (e.g., CI, Br), CN, NH$_2$, phenyl, etc.

Any anti-HER2 antibody, especially any Ig-like anti-HER2 antibody, may be used in the formation of the fusion protein of the present disclosure. The anti-HER2 antibody may be an isolated monoclonal antibody such as Trastuzumab and Margetuximab.

In some embodiments, the anti-HER2 antibody is an isolated monoclonal antibody comprising two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively. The Fab or paratope portion of the anti-HER2 antibody can bind to HER2 on the cell surfaces of cancer/tumor cells and thus prevent the occurring of uncontrolled growth of cancer/tumor cells, while the Fc portion of the anti-HER2 antibody can bind to FcRs on the cell surfaces of NK cells or macrophages to stimulate cancer cell killings by the NK cells or macrophages. In some embodiments, the heavy chain may comprise an amino acid sequence having at least 80%, 85%, 90%, 95%, 98% or 99% identity to SEQ ID NO: 6, wherein the anti-HER2 antibody is able to bind to HER2 and prevent the occurring of uncontrolled growth of cancer/tumor cells, and is also able to bind to FcRs on the cell surfaces of NK cells or macrophages and thus activate the NK cells or macrophages for killing the cancer cells. In some embodiments, the light chain may comprise an amino acid sequence having at least 80%, 85%, 90%, 95%, 98% or 99% identity to SEQ ID NO: 8, wherein the anti-HER2 antibody is able to bind to HER2 and prevent occurring of uncontrolled growth of cancer/tumor cells.

As described above, one or two copies of the SIRP extracellular Ig-like domain especially SIRPαD1 can be linked to either or each paratope of the anti-HER2 at the N-terminal of the heavy chain and/or the light chain constituting the specific paratope.

Also, the present disclosure provides a polynucleotide molecule encoding the recombinant fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present disclosure provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

In another aspect, the present disclosure provides a pharmaceutical composition comprising the fusion protein of the present disclosure formulated together with a pharmaceutically acceptable adjuvant. The composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the fusion protein can be administered as a sustained release formulation, in which case less frequent administration is required.

For administration of the fusion protein, the dosage ranges from about 0.0001 to 100 mg/kg, and more usually 0.01 to 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for the fusion protein of the disclosure include 3 mg/kg body weight or 6 mg/kg body weight via intraperitoneal administration, with the antibody being given using one of the following dosing schedules: (i) every four weeks for six dosages, then every three months; (ii) every three weeks; (iii) 3 mg/kg body weight once followed by 1 mg/kg body weight every three weeks; (vi) 6 mg/kg body weight, one dosage per week. In some methods, dosage is adjusted to achieve a plasma antibody concentration of about 1-1000 μg/ml and in some methods about 25-300 μg/ml.

A "therapeutically effective dosage" of a fusion protein of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a fusion protein of the present disclosure can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the fusion protein of the disclosure can be formulated to ensure proper distribution in vivo. For example, to ensure that the therapeutic fusion proteins of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331.

A gene therapy in vivo is also envisioned wherein a nucleic acid molecule encoding the recombinant fusion protein of the present disclosure, or a derivative thereof is introduced directly into the subject. For example, a nucleic acid sequence encoding a recombinant fusion protein of the present disclosure is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present disclosure is to provide a method for preparing the above recombinant fusion protein and the pharmaceutical composition comprising the same. In one embodiment, the method comprises (1) providing an protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present disclosure is to provide a method of treating cancer using the pharmaceutical composition of the present disclosure, comprising administrating an effective amount of the aforementioned pharmaceutical composition to the patients or subjects in need thereof. In one embodiment, the pharmaceutical composition is used to treat CD47 and/or HER2-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer and renal cancer.

In one embodiment, the diseases related to over-expressions of CD47 and/or HER2 include but are not limited to Crohn's disease, allergic asthma, and rheumatoid arthritis.

The present disclosure is now further described with the non-limiting examples below.

EXAMPLES

In the examples below, IMM29 refers to a HER2-specific antibody. This antibody has two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively.

IMM2901 is a recombinant fusion protein capable of binding to CD47 and HER2, containing two SIRPαD1s each linked via a GS-linker, to IMM29 at the N-terminus of each heavy chain, wherein the SIRPαD1 has an nucleic acid sequence and amino acid sequence of SEQ ID NO: 1 and SEQ ID NO: 2, respectively, and the linker having an amino acid sequence of SEQ ID NO: 4, which can be encoded by the nucleic acid sequence of SEQ ID NO: 3.

IMM2902 is also a recombinant fusion protein capable of binding to CD47 and HER2, and differs from IMM2901 in that each SIRPαD1 is linked via a GS-linker, to IMM29 at the N-terminus of each light chain.

IMM01 is a fusion protein capable of binding to CD47, consisting of SIRPαD1 linked to an Fc fragment, which was described in WO2016169261. The nucleic acid sequence and amino acid sequence of this fusion protein are set forth in SEQ ID NO: 13 and SEQ ID NO: 14, respectively.

IMM0404 is a recombinant fusion protein, containing two SIRPαD1s each linked via a GS-linker, to an anti-EGFR antibody at the N-terminus of each heavy chain. The SIRPαD1-GS-linker-anti-EGFR heavy chain has a nucleic acid sequence and amino acid sequence of SEQ ID NO: 15 and SEQ ID NO: 16, respectively. The light chain of the anti-EGFR antibody has an amino acid sequence of SEQ ID NO: 18, which may be encoded by nucleic acid sequences of SEQ ID NO: 17.

The structures of these proteins can be found in FIG. 1.

Example 1. Construction of Vectors Expressing IMM29, IMM2901, IMM2902, IMM01 and IMM0404

1.1 IMM29

The full-length coding sequence of IMM29 was designed artificially. Specifically, the coding sequences of both the heavy chain and the light chain variable regions were derived from Herceptin (Trastuzumab). 57 nucleotides encoding the signal peptide of mouse IgG1 heavy chain (SEQ ID NO.: 19) were added to the 5' end of the heavy chain-coding sequence (SEQ ID NO.: 5) or the light chain-coding sequence (SEQ ID NO.:7), and a Kozak sequence (SEQ ID NO.: 20) was added to the 5' end of the signal peptide sequence. Then, HindIII and NheI restriction sites were added to the 5' and 3' ends of the resulting heavy chain sequence, and HindIII and the XbaI restriction sites were added to the 5' and 3' ends of the resulting light chain sequence. The two resulting sequences were synthesized by Genscript (ID #: T84300 (heavy chain); T85555 (light chain)) and subcloned, respectively, into the pMac-H and pMac-L vectors.

1.2 IMM2901

The expression vector for the light chain of IMM2901 is identical to that of IMM29. For the heavy chain vector construction, the coding sequence of the first extracellular domain of SIRPα (SIRPαD1) (SEQ ID NO.:1) was linked through a GS-linker (SEQ ID NO.:3) to the N terminal of the heavy chain coding sequence of IMM29 (SEQ ID NO.:5) (totally SEQ ID NO.: 9). 57 nucleotides encoding the signal peptide of mouse IgG1 heavy chain (SEQ ID NO.:19) were added to the 5' end of SIRPαD1-coding sequence, and a Kozak sequence (SEQ ID NO.:20) was added to the 5' end of the signal peptide sequence. Lastly, HindIII and NheI restriction sites were added to the 5' and 3' ends of the resulting sequence, respectively. The resulting sequence was synthesized by Convenience Biology (ID #: Y0000506-1-A10863) and subcloned into the pMac-H vector.

1.3 IMM2902

The expression vector for the heavy chain of IMM2902 is identical to that of IMM29. For the light chain vector construction, the coding sequence of the first extracellular domain of SIRPα (SIRPαD1) (SEQ ID NO.:1) was linked through a GS-linker (SEQ ID NO.:3) to the N terminal of the light chain coding sequence of IMM29 (SEQ ID NO.:7) (totally SEQ ID NO.: 11). 57 nucleotides encoding the signal peptide of mouse IgG1 heavy chain (SEQ ID NO.:19) were added to the 5' end of SIRPαD1-coding sequence, and a Kozak sequence (SEQ ID NO.:20) was added to the 5' end of the signal peptide sequence. Lastly, HindIII and XbaI restriction sites were added to the 5' and 3' ends of the resulting sequence, respectively. The resulting sequence was synthesized by Convenience Biology (ID #: Y0000506-2-A10868) and subcloned into the pMac-L vector.

1.4 IMM01

The expression cassette of SIRPαD1-Fc was designed by sequentially connecting a Kozak sequence (SEQ ID NO.:20) with the coding sequence of the signal peptide (SEQ ID NO.:19) and SIRPαD1-Fc (SEQ ID NO.:13). HindIII and EcoRI restriction sites were respectively added to the 5' and 3' ends of the resulting sequence, which was synthesized by Convenience Biology (ID #: CN1418-F9043) and subcloned into the pMac-Fc vector.

1.5 IMM0404

The expression cassette for the light chain of IMM0404 was designed by sequentially connecting a Kozak sequence (SEQ ID NO.:20) with the coding sequence of the signal peptide (SEQ ID NO.:19) and the light chain of an anti-EGFR antibody (Erbitux (Cetuximab)) (SEQ ID NO.:17). HindIII and XbaI restriction sites were respectively added to the 5' and 3' ends of the resulting sequence, which was synthesized by Convenience Biology (ID #: NJ0719028J_A6315) and subcloned into the pMac-L vector. For the heavy chain vector construction, the coding sequence of the first extracellular domain of SIRPα (SIRPαD1) was linked through a GS-linker to the N terminal of the heavy chain coding sequence of an EGFR-specific antibody, the SIRPαD1-GS-linker-heavy chain was encoded by SEQ ID NO.:15. 57 nucleotides encoding the signal peptide of mouse IgG1 heavy chain (SEQ ID NO.:19) were added to the 5' end of SIRPαD1-GS-linker-heavy chain (SEQ ID NO.: 15), and a Kozak sequence (SEQ ID NO.:20) was added to the 5' end of the signal peptide sequence. Lastly, HindIII and NheI restriction sites were added to the 5' and 3' ends of the resulting sequence, which was synthesized by Genscript (ID #: M17025) and subcloned into the pMac-H vector.

Example 2. Protein Expression and Purification

To manufacture the desired proteins, the expression vectors of Example 1 were electroporated into Chinese Hamster Ovary (CHO) cells (ATCC, Cat #CCL-61) which were subjected to several rounds of pressure selection of neomycin. The selected stable cells were adapted to a serum-free Balan CD CHO Growth A medium (Irvine Scientific, Cat #94120). For protein expression, cells were seeded in a 3 L bioreactor and cultured in a fed-batch process. When the cell viability dropped to ~80%, reaction in the bioreactor was terminated, the cell culture supernatant was harvested and subjected to protein purification by affinity chromatography. The purity of recombinant protein was above 95%, and the content of endotoxin was below 0.5 U/g.

Example 3. IMM2901 and IMM2902 Bound to CD47 or HER2

CD47 or HER2 binding capacities of the recombinant proteins were measured by the enzyme-linked immunosorbent assay (ELISA). Recombinant Human CD47 (Lot #LC10DE2004, Sino Biologicals) and ErbB2 (Lot #LC11MC0201, Sino Biologicals) were, respectively, prepared in coating buffer (Product code: 1001329288 C3041-100CAP, Sigma-Aldrich Co.) and transferred to the ELISA plates (Cat #442404, Nunc™) at 50 ng/well. The plates were placed in 4° C. refrigerator overnight. When assays were performed, plates were washed for three times with PBS containing 0.05% of Tween-20 (PBS-T) before the titrated proteins were added, and the plates were incubated at room temperature for 1 hour. The plates were washed again for 5 times with PBS-T, and then HRP-Rabbit Anti-Human IgG Fc (Cat #:309-036-008, Jackson ImmunoResearch Lab) was added to the plates and incubated at room temperature for one hour. After the plates were washed for 5 times with PBS-T, and substrates were added to the plates which were read in a plate reader after the color changing was stopped by 1N H2SO4.

Figure 2:
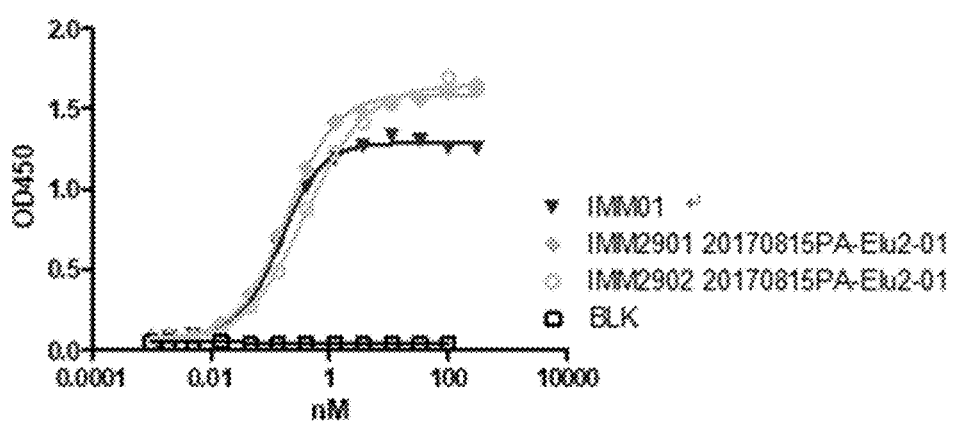
FIG. 2 shows the binding activities of IMM2901 and IMM2902 to CD47.
Figure 3:
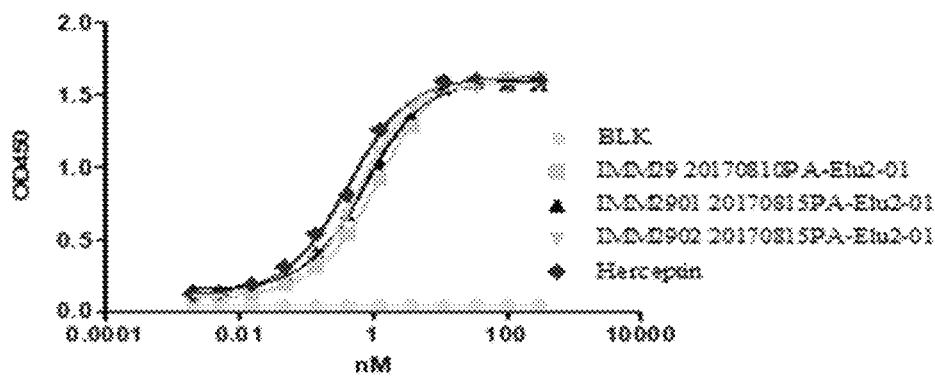
FIG. 3 shows the binding activities of IMM2901 and IMM2902 to HER2.

IMM2901 and IMM2902 bound to CD47 with an $EC_{50}$ value of 0.1903 nM and 0.3894, respectively (FIG. 2), and bound to HER2 with an $EC_{50}$ value of 0.7435 nM and 0.5931 nM, respectively (FIG. 3), a bit interior to the traditional single antigen targeting antibodies.

Example 4. IMM2902 Activated Phagocytosis of HL-60

Mouse macrophage cell line Ana-1 was seeded in a 96-well cell culture plate, $1 \times 10^5$ cells per well, and cultured for 16-18 hours at 37° C. and 5% $CO_2$. Target cells (HL-60) were labeled with CFSE, and then incubated with serially diluted IMM2902, or control proteins for 45 minutes. The target cell solutions containing the test proteins were transferred to the plate containing Ana-1 cells, the ratio of the number of Ana-1 cells to HL-60 cells was 1:3. The mixture was cultured for 2 hours at a cell culture incubator and then subject to FACS analysis for density of CFSE in Ana-1 cells.

Figure 4:
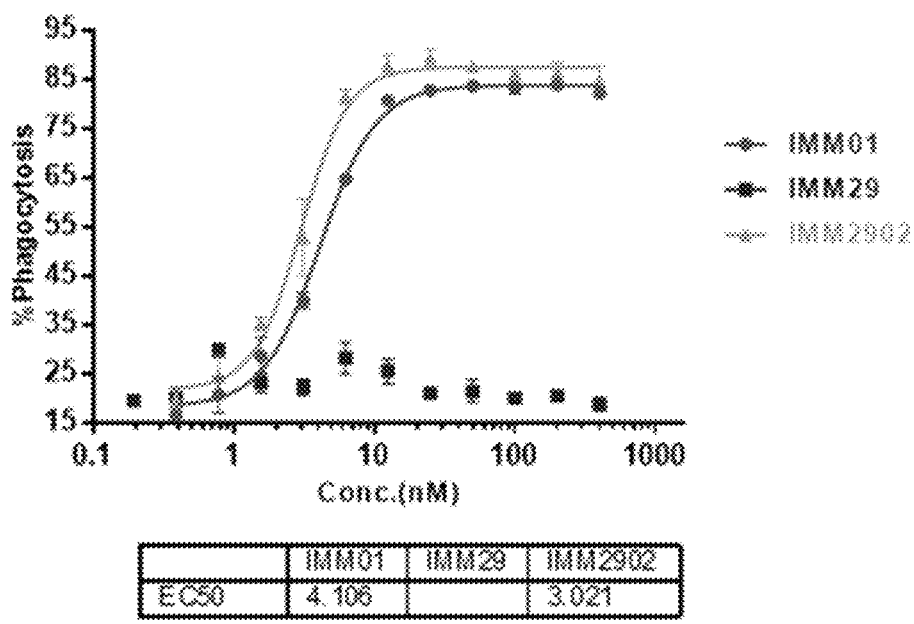
FIG. 4 shows IMM2902 induced phagocytosis of HL-60 cells.

As shown in FIG. 4, IMM2902 activated a high level of phagocytosis of tumor cells.

Example 5. IMM2902 had High Antibody-Dependent Cell-Mediated Cytotoxicity (ADCC)

CFSE-labeled BT-474 cells (used as target cells) were mixed with NK92MI cells (effector cells) stably expressing FcγRIIIa at a 1:2 ratio, and the mixed cells were cultured for 4 hours at 37° C. under 5% $CO_2$ in the presence of serially diluted IMM2902 or control proteins. Then 5 g/ml propidium iodide (PI) (Sigma, Cat #P4170) was added to the cell culture at a concentration of 5 μg/ml, and the cell culture was subjected to FACS analysis for PI signals. Percentage of cell lysis mediated by ADCC was calculated based on the following formula:

% Lysis=(% PI Positive Cell with IMM2902 or control proteins–% PI Positive Cell with negative control protein)/(100–% PI Positive Cell with negative control protein)*100

Figure 5:
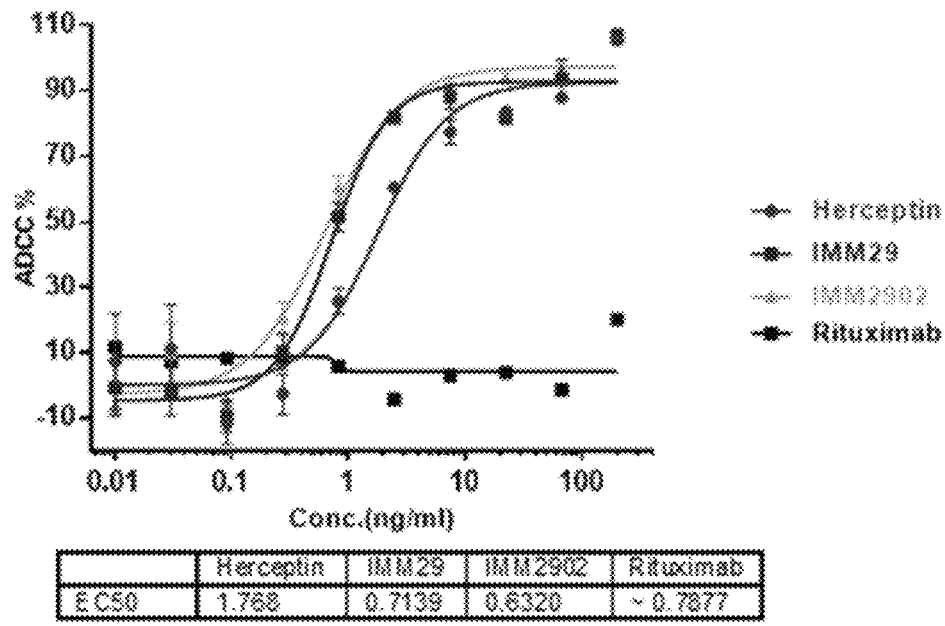
FIG. 5 shows IMM2902's ADCC activity.

As shown in FIG. 5, IMM2902 had a comparable or better ADCC activity compared to IMM29 and Herceptin.

Example 6. IMM2902 Induced HER2 Internalization $1 \times 10^6$ of BT-474 cells in 200 L of DMEM medium containing 5% of FBS were seeded in a 96-well cell culture plate and incubated at 37° C. and 5% $CO_2$ overnight. On the next day, the plate was taken out of the incubator and the medium was replaced with fresh medium containing titrated proteins. The plate was incubated for further 4 hours in the cell culture incubator before the cells were washed and stained with FITC-conjugated antibody specific for the Fc portion of human IgG. Percentage of HER2 receptor internalized was calculated based on the formula below:

Internalization Ratio=$(1-MFI/MFI_{t=0})*100\%$

MFI: mean fluorescence intensity

Figure 6:
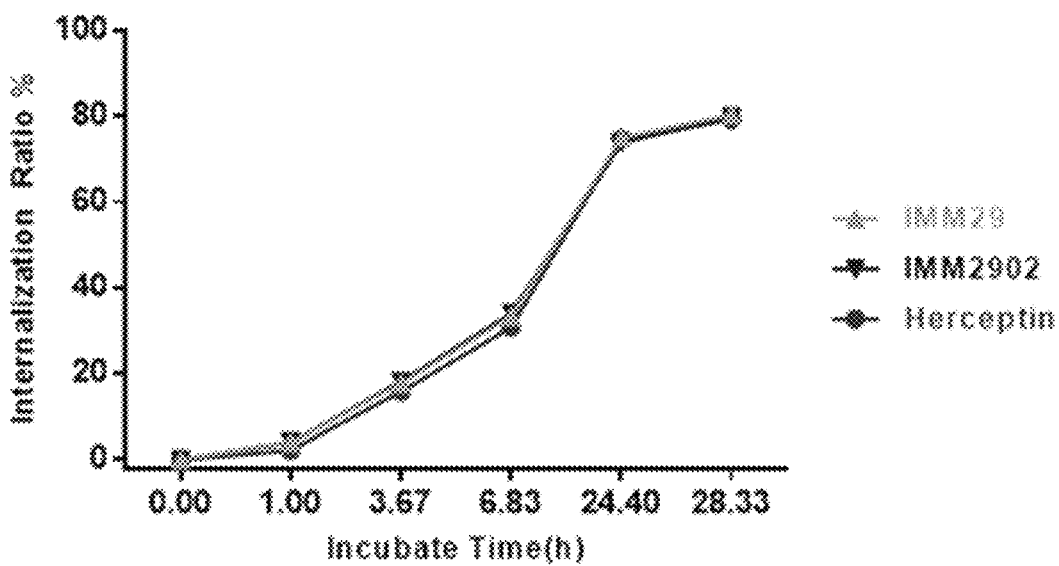
FIG. 6 shows IMM2902 induced HER2 internalization.

According to FIG. 6, IMM2902 was able to induce HER2 internalization in an equivalent level to IMM29 or Herceptin.

Example 7. IMM2902 had Good Anti-Tumor Effect

BT-474 human breast cancer cells (ATCC® Number: HTB-20; Lot number: 63087043) were cultured in a DMEM medium containing 10% FBS at 37° C. and 5% $CO_2$.

Cells were collected and re-suspended in a serum-free DMEM medium, $1 \times 10^8$/mL. The medium was added with and mixed with Matrigel at a volume ratio of 1:1 and then placed on ice for use.

Fifty-five nude mice were injected subcutaneously with BT-474 cells, $1 \times 10^7$ cells per mouse, at the right flank. These mice were given intramuscular injections of estrogens one week prior to tumor cell injection till the end of the test, three times a week (every Monday, Wednesday, and Friday), to keep growth of the estrogen-dependent tumor.

When tumor volume reached 100-150 mm³, 36 mice were randomly allocated into 6 groups with 6 mice in each group. Mice were respectively treated, twice a week, through intraperitoneal injection with PBS, IMM01 (3.0 mg/kg), Herceptin (5.0 mg/kg), IMM29 (5.0 mg/kg), IMM2909 (6.0 mg/kg), and IMM01+IMM29 (3.0 mg/kg+5.0 mg/kg), for 3 weeks. Totally six treatments were given. The day upon first dosing was defined as Day 0. Tumor volume and body weight were measured twice a week.

During treatments, if a mouse lost 15% or more of body weight, drug administration would be stopped until the weight loss became 10% or less. Animals were sacrificed when the average tumor volume in any group exceeded 2000 mm$^3$ or the experiment was completed.

The tumor volume (V) was calculated as (length×width$^2$)/2. Tumor growth inhibition rate (TGI) was calculated by the formula: Tumor growth inhibition rate=(1−tumor volume change in administration group/tumor volume change in control group)×100%. Dunnett's multi-comparison test was used to calculate group differences.

TABLE 1

Anti-tumor effect of IMM2902 and other antibodies

| Group | Drug | Animal# | Dose (mg/kg) | Treatment | TGI* |
|---|---|---|---|---|---|
| 1 | PBS | 6 | N/A | i.p, b.i.w × 3 | |
| 2 | IMM01 | 6 | 3.0 | i.p, b.i.w × 3 | 25.46% |
| 3 | Herceptin | 6 | 5.0 | i.p, b.i.w × 3 | 86.95% |
| 4 | IMM29 | 6 | 5.0 | i.p, b.i.w × 3 | 104.23% |
| 5 | IMM2902 | 6 | 6.0 | i.p, b.i.w × 3 | 115.28% |
| 6 | IMM01 + IMM29 | 6 | 3.0 + 5.0 | i.p, b.i.w × 3 | 110.88% |

Figure 7:
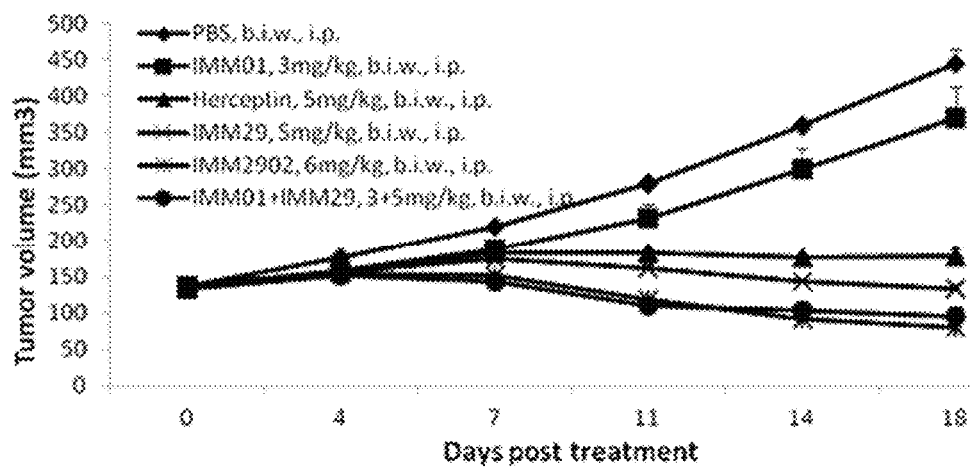
FIG. 7 shows in vivo therapeutic efficacy of IMM2902 in BT-474 xenograft model.

Group 5 had a tumor growth inhibition rate (TGI) of 115.28%, higher than those of other groups, as shown in Table 1 above and FIG. 7, suggesting IMM2902's better efficacy compared to the single antigen targeting antibodies. Especially, the TGI in group 5 was even higher than that of the group with combined use of IMM01 and IMM29.

Example 8. IMM0404's Anti-Tumor Activity in HT-29 or NCI-H1975 Xenograft Model 8.1 HT-29 Xenograft Model HT-29 human colon cancer cells were cultured in the McCoy's 5A medium containing 10% FBS at 37° C. and 5% CO$_2$.

Cells at the logarithmic phase were collected and re-suspended in 1×PBS. The suspension was added with and mixed with Matrige at a volume ratio of 1:1, and the mixture contained 3×10$^7$ cells per mL.

Forty mice were injected subcutaneously with HT-29 cells, 3×10$^6$ cells per mouse, at the right flank. When tumor volume reached 100-200 mm$^3$, these animals were randomly allocated into 5 groups with 8 mice in each group. Mice were respectively treated, once per week, through intraperitoneal injection with PBS, IMM01 (1.2 mg/kg), Erbitux (2.0 mg/kg), IMM0404 (2.7 mg/kg), and IMM01+Erbitux (1.2 mg/kg+2.0 mg/kg), for 4 weeks. Totally four treatments were given. The day upon first dosing was defined as Day 0. Tumor volume and body weight were measured twice a week.

The tumor volume (V) was calculated as (length×width$^2$)/2. Tumor growth inhibition rate (TGI) was calculated by the formula: Tumor growth inhibition rate=(1−tumor volume change in administration group/tumor volume change in control group)×100%. The student test was used to calculate group differences.

TABLE 2

Anti-tumor effect of IMM0404 and other antibodies

| Group | Drug | Animal# | Dose (mg/kg) | Treatment | TGI* |
|---|---|---|---|---|---|
| 1 | PBS | 8 | N/A | i.p, q.w. × 4 | |
| 2 | IMM01 | 8 | 1.2 | i.p, q.w. × 4 | 32.79% |
| 3 | Erbitux | 8 | 2.0 | i.p, q.w. × 4 | 40.00% |
| 4 | IMM0404 | 8 | 2.7 | i.p, q.w. × 4 | 18.48% |
| 5 | IMM01 + Erbitux | 8 | 1.2 + 2.0 | i.p, q.w. × 4 | 33.04% |

Figure 8:
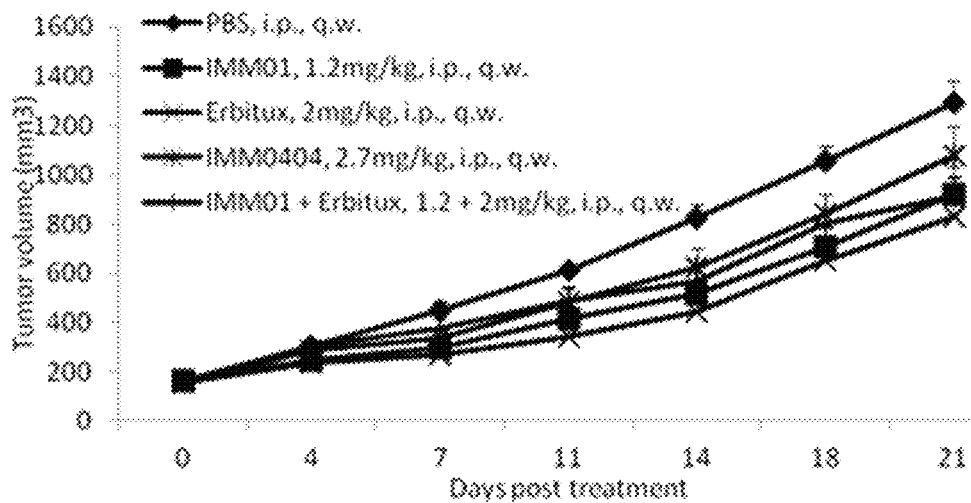
FIG. 8 shows in vivo therapeutic efficacy of IMM0404 in HT-29 xenograft model.

It can be seen from Table 2 and FIG. 8 that IMM0404 did not show better anti-tumor activity than other proteins in this xenograft model.

8.2 NCI-H1975 Xenograft Model

NCI-H1975 non-small cell lung cancer cells were cultured in the RPMI-1640 medium containing 10% FBS (GIBCO, US) at 37° C. and 5% CO$_2$.

Cells at the logarithmic phase were collected and re-suspended in 1×PBS, 1×10$^7$ cells per mL.

Forty SCID mice were injected subcutaneously with NCI-H1975 cells, 1×10$^6$ cells per mouse, at the right flank. When tumor volume reached 100-200 mm$^3$, these animals were randomly allocated into 5 groups with 8 mice in each group. Mice were respectively treated, once per week, through intraperitoneal injection with PBS, IMM01 (2.7 mg/kg), Erbitux (5.0 mg/kg), IMM0404 (6.0 mg/kg), and IMM01+Erbitux (2.7 mg/kg+5.0 mg/kg), for 3 weeks. Totally three treatments were given. The day upon first dosing was defined as Day 0. Tumor volume and body weight were measured twice a week.

The tumor volume (V) was calculated as (length×width$^2$)/2. Tumor growth inhibition rate (TGI) was calculated by the formula: Tumor growth inhibition rate=(1−tumor volume change in administration group/tumor volume change in control group)×100%. The student test was used to calculate group differences.

TABLE 3

Anti-tumor effect of IMM0404 and other antibodies

| Group | Durg | Animal# | Dose (mg/kg) | Treatment | TGI* |
|---|---|---|---|---|---|
| 1 | PBS | 8 | N/A | i.p, q.w. × 3 | |
| 2 | IMM01 | 8 | 2.7 | i.p, q.w. × 3 | 49.49% |
| 3 | Erbitux | 8 | 5.0 | i.p, q.w. × 3 | 85.69% |
| 4 | IMM0404 | 8 | 6.0 | i.p, q.w. × 3 | 68.77% |
| 5 | IMM01 + Erbitux | 8 | 2.7 + 5.0 | i.p, q.w. × 3 | 76.03% |

Figure 9:
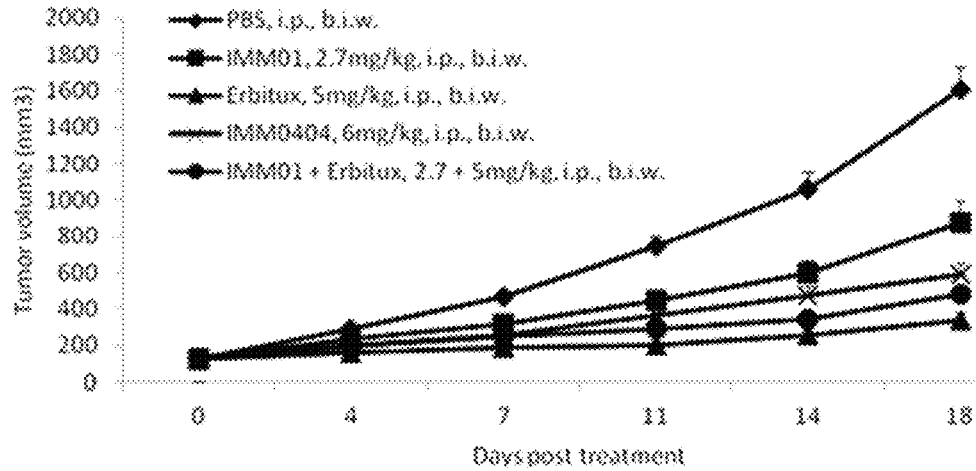
FIG. 9 shows in vivo therapeutic efficacy of IMM0404 in NCI-H1975 xenograft model.

It can be seen from Table 3 and FIG. 9 that IMM0404's anti-tumor activity was better than IMM01, but interior to Erbitux and IMM01+ Erbitux.

The data in this Example suggested that the bispecific antibodies do not necessarily show superior efficacy compared to the single antigen targeting antibodies.

While the invention has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

```
First extracellular Ig-like domain of SIRPalpha
                                        SEQ ID NO: 1
GAGGAGGAGC TGCAGGTGAT TCAGCCTGAC AAGTCCGTAT

CAGTTGCAGC TGGAGAGTCG GCCATTCTGC ACTGCACTGT

GACCTCCCTG ATCCCTGTGG GGCCCATCCA GTGGTTCAGA

GGAGCTGGAC CAGCCCGGGA ATTAATCTAC AATCAAAAAG

AAGGCCACTT CCCCCGGGTA CAACTGTTT CAGAGTCCAC

AAAGAGAGAA AACATGGACT TTTCCATCAG CATCAGTGCC

ATCACCCCAG CAGATGCCGG CACCTACTAC TGTGTGAAGT

TCCGGAAAGG GAGCCCTGAC ACGGAGTTTA AGTCTGGAGC

AGGCACTGAG CTGTCTGTGC GTGCCAAACC CTCTGCCCCC

GTGGTATCGG GCCCT 375
First extracellular Ig-like domain of SIRPalpha
                                        SEQ ID NO: 2
EEELQVIQPD KSVSVAAGES AILHCTVTSL IPVGPIQWFR

GAGPARELIY NQKEGHFPRV TTVSESTKRE NMDFSISISA

ITPADAGTYY CVKFRKGSPD TEFKSGAGTE LSVRAKPSAP

VVSGP 125
Linker
                                        SEQ ID NO: 3
GGCGG CGGTGGGAGC GGCGGCGGTG GGAGCGGCGG CGGGGGCTCG 45
Linker
                                        SEQ ID NO: 4
GGGGSGGGGS GGGGS 15
Heavy chain of anti-HER2 antibody
                                        SEQ ID NO: 5
GAGGTGCAGC TGGTCGAGAG CGGCGGGGGC CTCGTGCAGC

CGGGCGGGTC GCTGCGGCTG AGCTGCGCCG CGAGCGGGTT

CAACATCAAG GACACCTACA TCCACTGGGT GCGCCAGGCC

CCCGGCAAGG GCCTCGAGTG GGTCGCCCGG ATCTACCCCA

CGAACGGGTA CACCCGCTAC GCCGACAGCG TGAAGGGCCG

GTTCACCATC AGCGCGGACA CCTCGAAGAA CACGGCCTAC

CTGCAGATGA ACAGCCTGCG CGCCGAGGAC ACCGCCGTGT

ACTACTGCAG CCGGTGGGGC GGCGACGGGT TCTACGCCAT

GGACTACTGG GGGCAGGGCA CCCTCGTCAC CGTGAGCAGC

GCTAGCACCA AGGGCCCATC GGTCTTCCCC CTGGCACCCT

CCTCCAAGAG CACCTCTGGG GGCACAGCGG CCCTGGGCTG

CCTGGTCAAG GACTACTTCC CCGAACCGGT GACGGTGTCG

TGGAACTCAG GCGCCCTGAC CAGCGGCGTG CACACCTTCC

CGGCTGTCCT ACAGTCCTCA GGACTCTACT CCCTCAGCAG

CGTGGTGACC GTGCCCTCCA GCAGCTTGGG CACCCAGACC

TACATCTGCA ACGTGAATCA CAAGCCCAGC AACACCAAGG

TGGACAAGAG AGTTGAGCCC AAATCTTGTG ACAAAACTCA

CACATGCCCA CCGTGCCCAG CACCTGAACT CCTGGGGGGA

CCGTCAGTCT TCCTCTTCCC CCCAAAACCC AAGGACACCC

TCATGATCTC CCGGACCCCT GAGGTCACAT GCGTGGTGGT

GGACGTGAGC CACGAAGACC CTGAGGTCAA GTTCAACTGG

TATGTGGACG GCGTGGAGGT GCATAATGCC AAGACAAAGC

CGCGGGAGGA GCAGTACAAC GCCACGTACC GTGTGGTCAG

CGTCCTCACC GTCCTGCACC AAGACTGGCT GAATGGCAAG

GAGTACAAGT GCAAGGTCTC CAACAAAGCC CTCCCAGCCC

CCATCGCCGC AACCATCTCC AAAGCCAAAG GGCAGCCCCG

AGAACCACAG GTGTACACCC TGCCCCCATC CCGGGAGGAG

ATGACCAAGA ACCAAGTCAG CCTGACCTGC CTGGTCAAAG

GCTTCTATCC CAGCGACATC GCCGTGGAGT GGGAGAGCAA

TGGGCAGCCG GAGAACAACT ACAAGACCAC GCCTCCCGTG

CTGGACTCCG ACGGCTCCTT CTTCCTCTAT TCCAAGCTCA

CCGTGGACAA GAGCAGGTGG CAGCAGGGGA ACGTCTTCTC

ATGCTCCGTG ATGCATGAGG CTCTGCACAA CCACTACACG

CAGAAGAGCC TCTCCCTGTC TCCGGGCAAA TGA 1353
Heavy chain of anti-HER2 antibody
                                        SEQ ID NO: 6
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDYW GQGTLVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

PSVFLFPPKP KDTLMISRTP EVTCVVVDVS HEDPEVKFNW

YVDGVEVHNA KTKPREEQYN ATYRVVSVLT VLHQDWLNGK

EYKCKVSNKA LPAPIAATIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPGK 450
Light chain of anti-HER2 antibody
                                        SEQ ID NO: 7
GACATCCAGA TGACCCAGAG CCCGTCGAGC CTGAGCGCCA

GCGTGGGCGA CCGGGTCACG ATCACCTGCC GCGCGAGCCA

GGACGTGAAC ACCGCCGTGG CCTGGTACCA GCAGAAGCCC

GGGAAGGCCC CCAAGCTCCT GATCTACTCG GCGAGCTTCC

TGTACAGCGG CGTCCCCAGC CGGTTCAGCG GGTCGCGCAG

CGGCACCGAC TTCACGCTCA CCATCAGCAG CCTGCAGCCG

GAGGACTTCG CCACCTACTA CTGCCAGCAG CACTACACCA

CGCCCCCCAC CTTCGGGCAG GGCACCAAGG TGGAGATCAA
```

-continued

```
GCGAACTGTG GCTGCACCAT CTGTCTTCAT CTTCCCGCCA

TCTGATGAGC AGTTGAAATC TGGAACTGCC TCTGTTGTGT

GCCTGCTGAA TAACTTCTAT CCCAGAGAGG CCAAAGTACA

GTGGAAGGTG GATAACGCCC TCCAATCGGG TAACTCCCAG

GAGAGTGTCA CAGAGCAGGA CAGCAAGGAC AGCACCTACA

GCCTCAGCAG CACCCTGACG CTGAGCAAAG CAGACTACGA

GAAACACAAA GTCTACGCCT GCGAAGTCAC CCATCAGGGC

CTGAGCTCGC CCGTCACAAA GAGCTTCAAC AGGGGAGAGT

GTTAG 645
```

Light chain of anti-HER2 antibody
SEQ ID NO: 8

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC 214
```

SIRP alpha D1-Linker-anti-HER2 heavy chain
SEQ ID NO: 9

```
GAGGAGGAGC TGCAGGTGAT TCAGCCTGAC AAGTCCGTAT

CAGTTGCAGC TGGAGAGTCG GCCATTCTGC ACTGCACTGT

GACCTCCCTG ATCCCTGTGG GGCCCATCCA GTGGTTCAGA

GGAGCTGGAC CAGCCCGGGA ATTAATCTAC AATCAAAAAG

AAGGCCACTT CCCCCGGGTA CAACTGTTTT CAGAGTCCAC

AAAGAGAGAA AACATGGACT TTTCCATCAG CATCAGTGCC

ATCACCCCAG CAGATGCCGG CACCTACTAC TGTGTGAAGT

TCCGAAAGGG GAGCCCTGAC ACGGAGTTTA AGTCTGGAGC

AGGCACTGAG CTGTCTGTGC GTGCCAAACC CTCTGCCCCC

GTGGTATCGG GCCCTGGCGG CGGTGGGAGC GGCGGCGGTG

GGAGCGGCGG CGGGGGCTCG GAGGTGCAGC TGGTCGAGAG

CGGCGGGGGC CTCGTGCAGC CGGGCGGGTC GCTGCGGCTG

AGCTGCGCCG CGAGCGGGTT CAACATCAAG GACACCTACA

TCCACTGGGT GCGCCAGGCC CCCGGCAAGG GCCTCGAGTG

GGTCGCCCGG ATCTACCCCA CGAACGGGTA CACCCGCTAC

GCCGACAGCG TGAAGGGCCG GTTCACCATC AGCGCGGACA

CCTCGAAGAA CACGGCCTAC CTGCAGATGA ACAGCCTGCG

CGCCGAGGAC ACCGCCGTGT ACTACTGCAG CCGGTGGGGC

GGCGACGGGT TCTACGCCAT GGACTACTGG GGGCAGGGCA

CCCTCGTCAC CGTGAGCAGC GCTAGCACCA AGGGCCCATC

GGTCTTCCCC CTGGCACCCT CCTCCAAGAG CACCTCTGGG

GGCACAGCGG CCCTGGGCTG CCTGGTCAAG GACTACTTCC

CCGAACCGGT GACGGTGTCG TGGAACTCAG GCGCCCTGAC

CAGCGGCGTG CACACCTTCC CGGCTGTCCT ACAGTCCTCA
```

-continued

```
GGACTCTACT CCCTCAGCAG CGTGGTGACC GTGCCCTCCA

GCAGCTTGGG CACCCAGACC TACATCTGCA ACGTGAATCA

CAAGCCCAGC AACACCAAGG TGGACAAGAG AGTTGAGCCC

AAATCTTGTG ACAAAACTCA CACATGCCCA CCGTGCCCAG

CACCTGAACT CCTGGGGGGA CCGTCAGTCT TCCTCTTCCC

CCCAAAACCC AAGGACACCC TCATGATCTC CCGGACCCCT

GAGGTCACAT GCGTGGTGGT GGACGTGAGC CACGAAGACC

CTGAGGTCAA GTTCAACTGG TATGTGGACG GCGTGGAGGT

GCATAATGCC AAGACAAAGC CGCGGGAGGA GCAGTACAAC

GCCACGTACC GTGTGGTCAG CGTCCTCACC GTCCTGCACC

AAGACTGGCT GAATGGCAAG GAGTACAAGT GCAAGGTCTC

CAACAAAGCC CTCCCAGCCC CCATCGCCGC AACCATCTCC

AAAGCCAAAG GCAGCCCCG AGAACCACAG GTGTACACCC

TGCCCCCATC CCGGGAGGAG ATGACCAAGA ACCAAGTCAG

CCTGACCTGC CTGGTCAAAG GCTTCTATCC CAGCGACATC

GCCGTGGAGT GGGAGAGCAA TGGGCAGCCG GAGAACAACT

ACAAGACCAC GCCTCCCGTG CTGGACTCCG ACGGCTCCTT

CTTCCTCTAT TCCAAGCTCA CCGTGGACAA GAGCAGGTGG

CAGCAGGGGA ACGTCTTCTC ATGCTCCGTG ATGCATGAGG

CTCTGCACAA CCACTACACG CAGAAGAGCC TCTCCCTGTC

TCCGGGCAAA TGA 1773
```

SIRP alpha D1-Linker-anti-HER2 heavy chain
SEQ ID NO: 10

```
EEELQVIQPD KSVSVAAGES AILHCTVTSL IPVGPIQWFR

GAGPARELIY NQKEGHFPRV TTVSESTKRE NMDFSISISA

ITPADAGTYY CVKFRKGSPD TEFKSGAGTE LSVRAKPSAP

VVSGPGGGS GGGGSGGGGS EVQLVESGGG LVQPGGSLRL

SCAASGFNIK DTYIHWVRQA PGKGLEWVAR IYPTNGYTRY

ADSVKGRFTI SADTSKNTAY LQMNSLRAED TAVYYCSRWG

GDGFYAMDYW GQGTLVTVSS ASTKGPSVFP LAPSSKSTSG

GTAALGCLVK DYFPEPVTVS WNSGALTSGV HTFPAVLQSS

GLYSLSSVVT VPSSSLGTQT YICNVNHKPS NTKVDKRVEP

KSCDKTHTCP PCPAPELLGG PSVFLFPPKP KDTLMISRTP

EVTCVVVDVS HEDPEVKFNW YVDGVEVHNA KTKPREEQYN

ATYRVVSVLT VLHQDWLNGK EYKCKVSNKA LPAPIAATIS

KAKGQPREPQ VYTLPPSREE MTKNQVSLTC LVKGFYPSDI

AVEWESNGQP ENNYKTTPPV LDSDGSFFLY SKLTVDKSRW

QQGNVFSCSV MHEALHNHYT QKSLSLSPGK 590
```

SIRP alpha D1-Linker-anti-HER2 light chain
SEQ ID NO: 11

```
GAGGAGGAGC TGCAGGTGAT TCAGCCTGAC AAGTCCGTAT

CAGTTGCAGC TGGAGAGTCG GCCATTCTGC ACTGCACTGT
```

```
GACCTCCCTG ATCCCTGTGG GGCCCATCCA GTGGTTCAGA
GGAGCTGGAC CAGCCCGGGA ATTAATCTAC AATCAAAAAG
AAGGCCACTT CCCCCGGGTA CAACTGTTTC AGAGTCCAC
AAAGAGAGAA AACATGGACT TTTCCATCAG CATCAGTGCC
ATCACCCCAG CAGATGCCGG CACCTACTAC TGTGTGAAGT
TCCGGAAAGG GAGCCCTGAC ACGGAGTTTA AGTCTGGAGC
AGGCACTGAG CTGTCTGTGC GTGCCAAACC CTCTGCCCCC
GTGGTATCGG GCCCTGGCGG CGGTGGGAGC GGCGGCGGTG
GGAGCGGCGG CGGGGGCTCG GACATCCAGA TGACCCAGAG
CCCGTCGAGC CTGAGCGCCA GCGTGGGCGA CCGGGTCACG
ATCACCTGCC GCGCGAGCCA GGACGTGAAC ACCGCCGTGG
CCTGGTACCA GCAGAAGCCC GGGAAGGCCC CCAAGCTCCT
GATCTACTCG GCGAGCTTCC TGTACAGCGG CGTCCCCAGC
CGGTTCAGCG GGTCGCGCAG CGGCACCGAC TTCACGCTCA
CCATCAGCAG CCTGCAGCCG GAGGACTTCG CCACCTACTA
CTGCCAGCAG CACTACACCA CGCCCCCCAC CTTCGGGCAG
GGCACCAAGG TGGAGATCAA GCGAACTGTG CTGCACCAT
CTGTCTTCAT CTTCCCGCCA TCTGATGAGC AGTTGAAATC
TGGAACTGCC TCTGTTGTGT GCCTGCTGAA TAACTTCTAT
CCCAGAGAGG CCAAAGTACA GTGGAAGGTG GATAACGCCC
TCCAATCGGG TAACTCCCAG GAGAGTGTCA CAGAGCAGGA
CAGCAAGGAC AGCACCTACA GCCTCAGCAG CACCCTGACG
CTGAGCAAAG CAGACTACGA GAAACACAAA GTCTACGCCT
GCGAAGTCAC CCATCAGGGC CTGAGCTCGC CCGTCACAAA
GAGCTTCAAC AGGGGAGAGT GTTAG 1065
SIRP alpha D1-Linker-anti-HER2 light chain
                                      SEQ ID NO: 12
EEELQVIQPD KSVSVAAGES AILHCTVTSL IPVGPIQWFR
GAGPARELIY NQKEGHFPRV TTVSESTKRE NMDFSISISA
ITPADAGTYY CVKFRKGSPD TEFKSGAGTE LSVRAKPSAP
VVSGPGGGS GGGGSGGGGS DIQMTQSPSS LSASVGDRVT
ITCRASQDVN TAVAWYQQKP GKAPKLLIYS ASFLYSGVPS
RFSGSRSGTD FTLTISSLQP EDFATYYCQQ HYTTPPTFGQ
GTKVEIKRTV AAPSVFIFPP SDEQLKSGTA SVVCLLNNFY
PREAKVQWKV DNALQSGNSQ ESVTEQDSKD STYSLSSTLT
LSKADYEKHK VYACEVTHQG LSSPVTKSFN RGEC 354
SIRP alpha D1-Fc
                                      SEQ ID NO: 13
GAGGAGGAGC TGCAGGTGAT TCAGCCTGAC AAGTCCGTAT
CAGTTGCAGC TGGAGAGTCG GCCATTCTGC ACTGCACTGT
GACCTCCCTG ATCCCTGTGG GGCCCATCCA GTGGTTCAGA
GGAGCTGGAC CAGCCCGGGA ATTAATCTAC AATCAAAAAG
AAGGCCACTT CCCCCGGGTA CAACTGTTTC AGAGTCCAC
AAAGAGAGAA AACATGGACT TTTCCATCAG CATCAGTGCC
ATCACCCCAG CAGATGCCGG CACCTACTAC TGTGTGAAGT
TCCGGAAAGG GAGCCCTGAC ACGGAGTTTA AGTCTGGAGC
AGGCACTGAG CTGTCTGTGC GTGCCAAACC CTCTGCCCCC
GTGGTATCGG GCCCTGCGGC GAGGGCCACA CCTCAGCACG
AATTCGAGCC CAAATCTTGT GACAAAACTC ACACATGCCC
ACCGTGCCCA GCACCTGAAC TCCTGGGGGG ACCGTCAGTC
TTCCTCTTCC CCCCAAAACC CAAGGACACC CTCATGATCT
CCCGGACCCC TGAGGTCACA TGCGTGGTGG TGGACGTGAG
CCACGAAGAC CCTGAGGTCA AGTTCAACTG GTACGTGGAC
GGCGTGGAGG TGCATAATGC CAAGACAAAG CCGCGGGAGG
AGCAGTACAA CAGCACGTAC CGTGTGGTCA GCGTCCTCAC
CGTCCTGCAC CAGGACTGGC TGAATGGCAA GGAGTACAAG
TGCAAGGTCT CCAACAAAGC CCTCCCAGCC CCCATCGAGA
AAACCATCTC AAAGCCAAA GGGCAGCCCC GAGAACCACA
GGTGTACACC CTGCCCCCAT CCCGGGATGA GCTGACCAAG
AACCAGGTCA GCCTGACCTG CCTGGTCAAA GGCTTCTATC
CCAGCGACAT CGCCGTGGAG TGGGAGAGCA ATGGGCAGCC
GGAGAACAAC TACAAGACCA CGCCTCCCGT GCTGGACTCC
GACGGCTCCT TCTTCCTCTA CAGCAAGCTC ACCGTGGACA
AGAGCAGGTG GCAGCAGGGG AACGTCTTCT CATGCTCCGT
GATGCATGAG GCTCTGCACA ACCACTACAC GCAGAAGAGC
CTCTCCCTGT CTCCGGGTTG A 1101
SIRP alpha D1-Fc
                                      SEQ ID NO: 14
EEELQVIQPD KSVSVAAGES AILHCTVTSL IPVGPIQWFR
GAGPARELIY NQKEGHFPRV TTVSESTKRE NMDFSISISA
ITPADAGTYY CVKFRKGSPD TEFKSGAGTE LSVRAKPSAP
VVSGPAARAT PQHEFEPKSC DKTHTCPPCP APELLGGPSV
FLFPPKPKDT LMISRTPEVT CVVVDVSHED PEVKFNWYVD
GVEVHNAKTK PREEQYNSTY RVVSVLTVLH QDWLNGKEYK
CKVSNKALPA PIEKTISKAK GQPREPQVYT LPPSRDELTK
NQVSLTCLVK GFYPSDIAVE WESNGQPENN YKTTPPVLDS
DGSFFLYSKL TVDKSRWQQG NVFSCSVMHE ALHNHYTQKS
LSLSPG 366
SIRP alpha D1-Linker-anti-EGFR light chain
                                      SEQ ID NO: 15
GAGGAGGAGC TGCAGGTGAT TCAGCCTGAC AAGTCCGTAT
CAGTTGCAGC TGGAGAGTCG GCCATTCTGC ACTGCACTGT
GACCTCCCTG ATCCCTGTGG GGCCCATCCA GTGGTTCAGA
GGAGCTGGAC CAGCCCGGGA ATTAATCTAC AATCAAAAAG
AAGGCCACTT CCCCCGGGTA CAACTGTTTC AGAGTCCAC
```

-continued

```
AAAGAGAGAA AACATGGACT TTTCCATCAG CATCAGTGCC
ATCACCCCAG CAGATGCCGG CACCTACTAC TGTGTGAAGT
TCCGAAAGG GAGCCCTGAC ACGGAGTTTA AGTCTGGAGC
AGGCACTGAG CTGTCTGTGC GTGCCAAACC CTCTGGCGGC
GGTGGGAGCG GCGGCGGTGG GAGCGGCGGC GGGGGCTCGC
AGGTGCAGCT GAAGCAGTCA GGACCTGGCC TAGTGCAGCC
CTCACAGAGC CTGTCCATCA CCTGCACAGT CTCTGGTTTC
TCATTAACTA ACTATGGTGT ACACTGGGTT CGCCAGTCTC
CAGGAAAGGG TCTGGAGTGG CTGGGAGTGA TATGGAGTGG
TGGAAACACA GACTATAATA CACCTTTCAC ATCCAGACTG
AGCATCAACA AGGACAATTC CAAGAGCCAA GTTTTCTTTA
AAATGAACAG TCTGCAATCT CAGGACACAG CCATATATTA
CTGTGCCAGA GCCCTCACCT ACTATGATTA CGAGTTTGCT
TACTGGGGCC AAGGGACTCT GGTCACTGTC TCTGCAGCTA
GCACCAAGGG CCCATCGGTC TTCCCCCTGG CACCCTCCTC
CAAGAGCACC TCTGGGGGCA CAGCGGCCCT GGGCTGCCTG
GTCAAGGACT ACTTCCCCGA ACCGGTGACG GTGTCGTGGA
ACTCAGGCGC CCTGACCAGC GGCGTGCACA CCTTCCCGGC
TGTCCTACAG TCCTCAGGAC TCTACTCCCT CAGCAGCGTG
GTGACCGTGC CCTCCAGCAG CTTGGGCACC CAGACCTACA
TCTGCAACGT GAATCACAAG CCCAGCAACA CCAAGGTGGA
CAAGAGAGTT GAGCCCAAAT CTTGTGACAA AACTCACACA
TGCCCACCGT GCCCAGCACC TGAACTCCTG GGGGGACCGT
CAGTCTTCCT CTTCCCCCCA AAACCCAAGG ACACCCTCAT
GATCTCCCGG ACCCCTGAGG TCACATGCGT GGTGGTGGAC
GTGAGCCACG AAGACCCTGA GGTCAAGTTC AACTGGTATG
TGGACGGCGT GGAGGTGCAT AATGCCAAGA CAAAGCCGCG
GGAGGAGCAG TACAACGCCA CGTACCGTGT GGTCAGCGTC
CTCACCGTCC TGCACCAAGA CTGGCTGAAT GGCAAGGAGT
ACAAGTGCAA GGTCTCCAAC AAAGCCCTCC CAGCCCCCAT
CGCCGCAACC ATCTCCAAAG CCAAAGGGCA GCCCCGAGAA
CCACAGGTGT ACACCCTGCC CCCATCCCGG GAGGAGATGA
CCAAGAACCA AGTCAGCCTG ACCTGCCTGG TCAAAGGCTT
CTATCCCAGC GACATCGCCG TGGAGTGGGA GAGCAATGGG
CAGCCGGAGA ACAACTACAA GACCACGCCT CCCGTGCTGG
ACTCCGACGG CTCCTTCTTC CTCTATTCCA AGCTCACCGT
GGACAAGAGC AGGTGGCAGC AGGGGAACGT CTTCTCATGC
TCCGTGATGC ATGAGGCTCT GCACAACCAC TACACGCAGA
AGAGCCTCTC CCTGTCTCCG GGCAAATGA                1749
```

SIRP alpha D1-Linker-anti-EGFR light chain
SEQ ID NO: 16

```
EEELQVIQPD KSVSVAAGES AILHCTVTSL IPVGPIQWFR
GAGPARELIY NQKEGHFPRV TTVSESTKRE NMDFSISISA
ITPADAGTYY CVKFRKGSPD TEFKSGAGTE LSVRAKPSGG
GGSGGGGSGG GGSQVQLKQS GPGLVQPSQS LSITCTVSGF
SLTNYGVHWV RQSPGKGLEW LGVIWSGGNT DYNTPFTSRL
SINKDNSKSQ VFFKMNSLQS QDTAIYYCAR ALTYYDYEFA
YWGQGTLVTV SAASTKGPSV FPLAPSSKST SGGTAALGCL
VKDYFPEPVT VSWNSGALTS GVHTFPAVLQ SSGLYSLSSV
VTVPSSSLGT QTYICNVNHK PSNTKVDKRV EPKSCDKTHT
CPPCPAPELL GGPSVFLFPP KPKDTLMISR TPEVTCVVVD
VSHEDPEVKF NWYVDGVEVH NAKTKPREEQ YNATYRVVSV
LTVLHQDWLN GKEYKCKVSN KALPAPIAAT ISKAKGQPRE
PQVYTLPPSR EEMTKNQVSL TCLVKGFYPS DIAVEWESNG
QPENNYKTTP PVLDSDGSFF LYSKLTVDKS RWQQGNVFSC
SVMHEALHNH YTQKSLSLSP GK                       582
```

Light chain of anti-EGFR antibody
SEQ ID NO: 17

```
GACATCTTGC TGACTCAGTC TCCAGTCATC CTGTCTGTGA
GTCCAGGAGA AAGAGTCAGT TTCTCCTGCA GGGCCAGTCA
GAGTATTGGC ACAAACATAC ACTGGTATCA GCAAAGAACA
AATGGTTCTC CAAGGCTTCT CATAAAGTAT GCTTCTGAGT
CTATCTCTGG GATCCCTTCC AGGTTTAGTG GCAGTGGATC
AGGGACAGAT TTTACTCTTA GCATCAACAG TGTGGAGTCT
GAAGATATTG CAGATTATTA CTGTCAACAA AATAATAACT
GGCCAACCAC GTTCGGTGCT GGGACCAAGC TGGAGCTGAA
ACGAACTGTG GCTGCACCAT CTGTCTTCAT CTTCCCGCCA
TCTGATGAGC AGTTGAAATC TGGAACTGCC TCTGTTGTGT
GCCTGCTGAA TAACTTCTAT CCCAGAGAGG CCAAAGTACA
GTGGAAGGTG GATAACGCCC TCCAATCGGG TAACTCCCAG
GAGAGTGTCA CAGAGCAGGA CAGCAAGGAC AGCACCTACA
GCCTCAGCAG CACCCTGACG CTGAGCAAAG CAGACTACGA
GAAACACAAA GTCTACGCCT GCGAAGTCAC CCATCAGGGC
```

```
CTGAGCTCGC CCGTCACAAA GAGCTTCAAC AGGGGAGAGT

GTTAG                                                          645
```

Light chain of anti-EGFR antibody

SEQ ID NO: 18

```
DILLTQSPVI LSVSPGERVS FSCRASQSIG TNIHWYQQRT

NGSPRLLIKY ASESISGIPS RFSGSGSGTD FTLSINSVES

EDIADYYCQQ NNNWPTTFGA GTKLELKRTV AAPSVFIFPP

SDEQLKSGTA SVVCLLNNFY PREAKVQWKV DNALQSGNSQ
```

```
ESVTEQDSKD STYSLSSTLT LSKADYEKHK VYACEVTHQG

LSSPVTKSFN RGEC                                                214
``` signal peptide of mouse IgG1 heavy chain

SEQ ID NO: 19

```
ATGGGATGGT CATGTATCAT CCTTTTTCTG GTAGCAACTG

CAACTGGAGT ACATTCA                                              57
```

Kozak

SEQ ID NO: 20

```
GCCGCCACC                                                        9
```

We claim:

1. A recombinant fusion protein, comprising SEQ ID NO: 2, a linker comprising a peptide of 10 to 30 amino acid residues, and an anti-HER2 antibody, wherein every paratope of the anti-HER2 antibody is linked to SEQ ID NO: 2 at the N-terminus of the light chain constituting the paratope, and wherein the anti-HER2 antibody heavy chains comprise SEQ ID NO:6 and the anti-HER2 antibody light chains comprise SEQ ID NO:8, and the recombinant fusion protein is capable of blocking binding of CD47s on cancer cells to signal-regulatory proteins (SIRPs) on surfaces of macrophages, binding to HER2s on cancer cells to inhibit uncontrolled cancer cell growth, and binding to FcRs on NK cells or macrophages.

2. The recombinant fusion protein of claim 1, wherein the linker is -(Gly-Gly-Gly-Gly-Ser)$_3$- (SEQ ID NO: 4).

3. A polynucleotide encoding the recombinant fusion protein of claim 1.

4. An expression vector comprising the polynucleotide of claim 3.

5. A host cell comprising the expression vector of claim 4.

6. A pharmaceutical composition, comprising the recombinant fusion protein of claim 1, and at least one pharmaceutical carrier.

7. The recombinant fusion protein of claim 1, the anti-HER2 antibody is a monoclonal antibody.

8. The recombinant fusion protein of claim 7, wherein the anti-HER2 antibody is Trastuzumab.

9. A method for treating a cancer, wherein cells of the cancer over-express CD47 and/or HER2, comprising administering to a patient or a subject a therapeutically effective amount of the pharmaceutical composition of claim 6.

10. The method of claim 9, wherein the cancer is selected from the group consisting of acute myelocytic leukemia (AML), chronic myelocytic leukemia (CIVIL), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, and renal cell carcinoma.

* * * * *